(12) United States Patent
Nadeau

(10) Patent No.: US 9,315,863 B2
(45) Date of Patent: Apr. 19, 2016

(54) SEQUENCE-SPECIFIC METHODS FOR HOMOGENEOUS, REAL-TIME DETECTION OF LAMP PRODUCTS

(75) Inventor: James G. Nadeau, Ellicott City, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 747 days.

(21) Appl. No.: 13/505,598

(22) PCT Filed: Nov. 4, 2010

(86) PCT No.: PCT/US2010/055392
§ 371 (c)(1),
(2), (4) Date: Jul. 18, 2012

(87) PCT Pub. No.: WO2011/056933
PCT Pub. Date: May 12, 2011

(65) Prior Publication Data
US 2012/0276538 A1 Nov. 1, 2012

Related U.S. Application Data

(60) Provisional application No. 61/258,404, filed on Nov. 5, 2009.

(51) Int. Cl.
*C12Q 1/68* (2006.01)

(52) U.S. Cl.
CPC .................................. *C12Q 1/6865* (2013.01)

(58) Field of Classification Search
CPC .................. C12Q 1/6865; C12Q 2525/307
USPC .......................................................... 435/91.2
See application file for complete search history.

(56) References Cited

U.S. PATENT DOCUMENTS

| 6,316,200 | B1 | 11/2001 | Nadeau et al. |
| 2003/0207292 | A1 | 11/2003 | Notomi et al. |
| 2006/0160084 | A1 | 7/2006 | Mitani et al. |
| 2007/0238113 | A1 | 10/2007 | Kanda et al. |
| 2008/0009420 | A1 | 1/2008 | Schroth et al. |

FOREIGN PATENT DOCUMENTS

| EP | 0678582 A1 | 10/1995 |
| JP | H07-289299 A | 11/1995 |
| JP | 2002045192 A | 2/2002 |
| WO | 0177317 A1 | 10/2001 |
| WO | 2009063243 A2 | 5/2009 |

OTHER PUBLICATIONS

Extended European Search Report for Applicaiton EP10829068 dated Apr. 22, 2013.
Inernational Search Report for Application No. PCT/US2010/055392 dated Apr. 11, 2011.
Iwamoto et al., Loop-mediated isothermal amplification for direct detection of *Mycobacterium tuberculosis* complex, M. avium, and M. intracellulare in sputum samples, Journal of Clinical Microbiology, American Society for Microbiology, Washington, DC, US, vol. 41, No. 6, Jun. 1, 2003, pp. 2616-2622, XP002450534.
Notomi et al, "Loop-mediated isothermal amplification of DNA", Nucleic Acids Research, Oxford University Press, Surrey, GB, vol. 28, No. 12, (2000), pp. i-vii, XP007905272.

*Primary Examiner* — Cynthia B Wilder
(74) *Attorney, Agent, or Firm* — Lerner, David, Littenberg, Krumholz & Mentlik, LLP

(57) ABSTRACT

Presented herein are methods and compositions for generating sequence-specific, secondary amplification products during Loop-mediated Isothermal Amplification (LAMP). Conventional LAMP produces a preponderance of high molecular weight DNA structures concatenated into self-complementary hairpins, which are not amenable to detection by routine probe-based hybridization methods, making multiplex detection of two or more targets or sequence variants in closed-tube formats extremely difficult. Provided herein, for example, are methods for generating secondary LAMP products bearing a fragment of the original target sequence embedded within low-molecular weight products that are devoid of competitive hairpin structures, the lack of which enhances probe-based detection of target sequences. These secondary products can, for example, be produced in real-time, during the LAMP process, and can provide the option of detecting multiple target sequences within a single tube using, e.g., a homogenous, real-time fluorescence format.

29 Claims, 13 Drawing Sheets

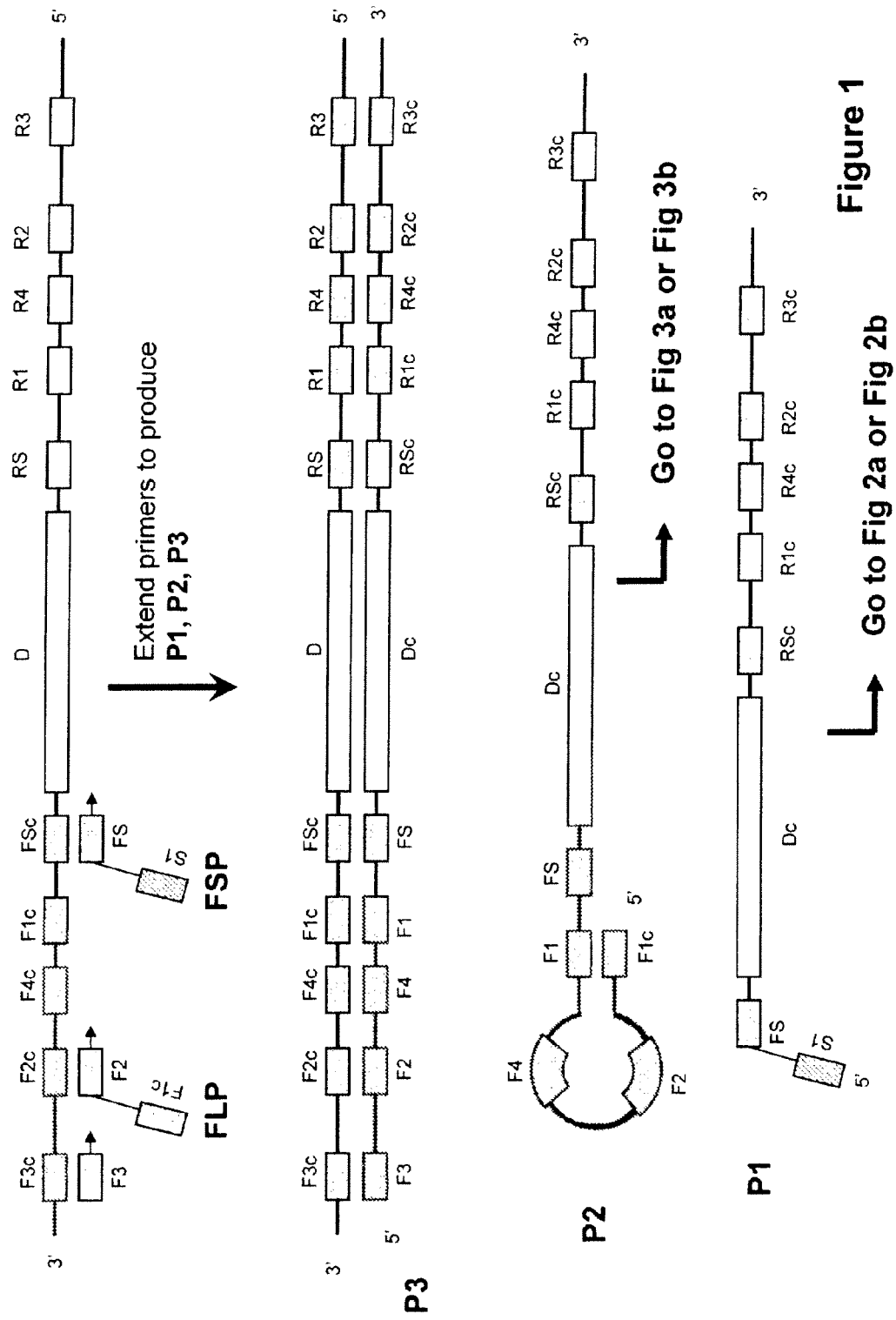

SEQUENCE-SPECIFIC METHODS FOR HOMOGENEOUS, REAL-TIME DETECTION OF LAMP PRODUCTS

CROSS-REFERENCE TO RELATED APPLICATIONS

This application is a national phase entry under 35 U.S.C. §371 of International Application No. PCT/US2010/055392 filed Nov. 4, 2010 published in English as International Publication No. WO 2011/056933, which claims priority of U.S. Provisional Application No. 61/258,404, filed Nov. 5, 2009, all of which are incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Apr. 12, 2012, is named Sequence_Listing_text_format.txt and is 10,703 bytes in size.

1. Field

The present methods relate, in one aspect, to improved methods for real-time sequence-specific detection of target sequences generated using Loop-mediated Isothermal Amplification (LAMP).

2. Background

Nucleic acid amplification is one of the most valuable tools in clinical medicine, for example for diagnosis of infectious diseases, genetic disorders and genetic traits. LAMP is a simple, rapid, specific and cost-effective nucleic acid amplification method (see U.S. Pat. Nos. 6,974,670 and 6,410,278). Unlike amplification methods such as PCR, LAMP may be conducted under isothermal conditions, eliminating the need for heat denaturation of double-stranded DNA products to promote the next round of DNA synthesis (see Notomi et al., Nucl. Acid Res. 28(12): e63 (2000) (hereinafter "Notomi et al.")). Further unlike amplification methods like NASBA (nucleic acid sequence-based amplification) or SDA (strand displacement amplification), LAMP doesn't require use of any enzymes in addition to the strand-displacement DNA polymerase, which makes it more cost-effective. Conventional LAMP produces a preponderance of high-molecular weight DNA, however, containing numerous copies of the original target sequence concatenated into self-complementary hairpin structures, which, because of their high melting temperatures and strong tendency to fold on themselves, are not amenable to detection by routine probe-based hybridization methods, such as Molecular beacons.

There exists, therefore, a need for improvements in sequence detection using LAMP.

3. SUMMARY

In one aspect, presented herein are methods and compositions that allow real-time, sequence-specific, detection, e.g., multiplex detection, of a nucleic acid sequence within a target nucleic acid molecule by utilizing one or more signal primers or primer pairs in conjunction with a loop-mediated isothermal amplification ("LAMP") reaction to generate a nucleic acid detection product comprising a target nucleic acid molecule portion of interest, or a complement thereof, wherein the nucleic acid detection product does not comprise a hairpin nucleic acid sequence or structure, thereby making the nucleic acid detection product particularly amenable to detection. For example, the nucleic acid detection product can be detected by conventional hybridization of reporter probes or by incorporating a reporter group into one or more signal primers.

In another aspect, presented herein are methods and compositions that allow real-time, sequence-specific, multiplex detection of two or more nucleic acid sequences within one, two, or more target nucleic acid molecules by utilizing signal primers or primer pairs in conjunction with a LAMP reaction to generate nucleic acid detection products comprising nucleic acid target portion of interest, or complements thereof, wherein the nucleic acid detection products do not comprise a hairpin nucleic acid sequence or structure, thereby making the nucleic acid detection products particularly amenable to detection.

For example, a nucleic acid detection product or products can be detected by conventional hybridization of reporter probes or by incorporating a reporter group into one or more signal primers. In addition, the nucleic acid detection products can, for example, be produced in real-time, in conjunction with, e.g., during, the LAMP process, and provide the option of detecting multiple nucleic acid detection products within a single reaction vessel, e.g., tube, using, for example, a real-time fluorescence format.

In one embodiment, presented herein is a method for generating a nucleic acid signal extension product during a loop-mediated isothermal amplification reaction, comprising:

(a) hybridizing a nucleic acid signal primer to a region of a nucleic acid target sequence, wherein said target sequence comprises at least one self-complementary hairpin structure generated during a loop-mediated isothermal amplification reaction, and wherein said region is not situated in a loop region of the hairpin structure; and (b) extending the hybridized nucleic acid signal primer on the nucleic acid target sequence to produce a first signal extension product, wherein said first signal extension product comprises one hairpin structure.

The above-described method, may further comprise detecting the first signal extension product. In one embodiment, the signal primer comprises a hybridization region and a reporter region, wherein the hybridization region hybridizes to the region of the nucleic acid target sequence, and wherein the reporter region produces a fluorescent signal.

In another embodiment, presented herein is a method for generating nucleic acid signal extension products during a loop-mediated isothermal amplification reaction, comprising:

(a) hybridizing a nucleic acid signal primer to a nucleic acid target sequence region, wherein the target sequence comprises at least one self-complementary hairpin structure generated during a loop-mediated isothermal amplification reaction;

(b) extending the hybridized nucleic acid signal primer on the nucleic acid target sequence to produce a first signal extension product, wherein said first signal extension product comprises a hairpin structure;

(c) hybridizing a nucleic acid amplification primer to a loop region of the first signal extension product, and extending the hybridized nucleic acid amplification primer on the first signal extension product to produce a second signal extension product and a third signal extension product, wherein the second signal extension product lacks a hairpin structure; and wherein the third signal extension product has a hairpin structure on its 5' end.

In another embodiment, presented herein is a method for generating a nucleic acid signal product during a loop-mediated isothermal amplification reaction, comprising:

(a) hybridizing a nucleic acid signal primer to a nucleic acid target sequence region, wherein the target sequence comprises at least one self-complementary hairpin structure generated during a loop-mediated isothermal amplification reaction;

(b) extending the hybridized nucleic acid signal primer on the nucleic acid target sequence to produce a first signal extension product, wherein said first signal extension product comprises a hairpin structure;

(c) hybridizing a nucleic acid amplification primer to a loop region of the first signal extension product, and extending the hybridized nucleic acid amplification primer on the first signal extension product to produce a second signal extension product, wherein the second signal extension product is double-stranded and lacks a hairpin structure; and (d) hybridizing a nucleic acid signal primer to the second signal extension product, and extending the hybridized nucleic acid signal primer on the second signal extension product to produce a third signal extension product, wherein the third signal extension product has a hairpin structure on its 5' end.

The above-described methods may further comprise detecting the second and/or the third signal extension products.

In yet another embodiment, the present presented herein is a method for concurrently generating nucleic acid signal extension products during a loop-mediated isothermal amplification reaction, comprising:

(a) hybridizing a nucleic acid signal primer to a nucleic acid target sequence region, wherein the target sequence comprises at least one self-complementary hairpin structure generated during a loop-mediated isothermal amplification reaction;

(b) extending the hybridized nucleic acid signal primer on the nucleic acid target sequence to produce a first signal extension product, wherein said first signal extension product comprises a hairpin structure;

(c) hybridizing a nucleic acid amplification primer to a loop region of the first signal extension product, and extending the hybridized nucleic acid amplification primer on the first signal extension product to produce a second signal extension product and a third signal extension product, wherein the second signal extension product lacks a hairpin structure; and wherein the third signal extension product is single-stranded and has a hairpin structure on its 5' end; and (d) hybridizing the nucleic acid signal primer to the third signal extension product, and extending the hybridized nucleic acid signal primer on the third signal extension product to produce a fourth signal extension product, wherein the fourth signal extension product comprises double-stranded nucleic acid.

In another embodiment, presented herein is a method for generating nucleic acid signal products during a loop-mediated isothermal amplification reaction, comprising:

(a) hybridizing a nucleic acid signal primer to a nucleic acid target sequence region, wherein the target sequence comprises at least one self-complementary hairpin structure generated during a loop-mediated isothermal amplification reaction;

(b) extending the hybridized nucleic acid signal primer on the nucleic acid target sequence to produce a first signal extension product, wherein said first signal extension product comprises a hairpin structure;

(c) hybridizing a nucleic acid amplification primer to a loop region of the first signal extension product, and extending the hybridized nucleic acid amplification primer on the first signal extension product to produce a second signal extension product, wherein the second signal extension product is double stranded and lacks a hairpin structure;

(d) hybridizing a nucleic acid signal primer to the second signal extension product, and extending the hybridized nucleic acid signal primer on the second signal extension product to produce a third signal extension product, wherein the third signal extension product is single stranded and has a hairpin structure on its 5' end; and (e) hybridizing the nucleic acid signal primer to the third signal extension product, and extending the hybridized nucleic acid signal primer on the third signal extension product to produce a fourth signal extension product, wherein the fourth signal extension product comprises double-stranded nucleic acid.

In one embodiment, the above-described methods further comprise detecting the fourth signal extension product.

In certain embodiment of the methods presented herein, two or more target sequences or sequence variants are used concurrently, wherein two or more nucleic acid signal primers which hybridize to said two or more target sequences are used. In one embodiment, the two or more target sequences are sequences are present in the same contiguous nucleotide sequence or on two different nucleotide sequences. In another embodiment, the two or more target sequences or sequence variants are derived from one organism or from two or more different organisms. In some embodiments, the first, second, third, or fourth signal extension product is detected in real-time. In certain embodiments, the first, second, third, or fourth signal extension product is detected in a closed tube format. In other embodiments, the first, second, third, or fourth signal extension product is detected post-amplification.

In one embodiment, the first, second, third, or fourth signal extension product is detected by a hybridization probe. In one such embodiment, the hybridization probe is a single nucleotide difference sensitive probe. In another embodiment, hybridization probe is fluorogenic. In a specific embodiment, the hybridization probe is a Molecular beacon. In another specific embodiment, the first, second, third, or fourth signal extension product is detected using a fluorogenic probe or SERS-labeled probe.

In certain embodiments of the methods of the present presented herein, the signal primer comprises a hybridization region and a reporter region, wherein the hybridization region hybridizes to a region of the nucleic acid target sequence, and wherein the first, second, third, or fourth signal extension product is detected by means of the reporter region. In one embodiment, the reporter group produces a fluorescent signal. In another embodiment, the reporter group is a fluorogenic hairpin. In yet another embodiment, the first, the second, the third, or the fourth signal extension product is detected by means of a modification to facilitate capture of the signal product incorporated into one of the signal primers.

In one embodiment, presented herein is a method for generating a nucleic acid detection product, comprising:
 combining a target nucleic acid molecule and primer nucleic acids F3, FLP, FSP, RLP, RSP, and R3 under conditions that allow complementary nucleic acids to hybridize and nucleic acid extension reactions to occur, wherein:
 (i) the target nucleic acid and each of the primer nucleic acids comprises a 5' terminus ("5'") and a 3' terminus ("3'");
 (ii) each of the primer nucleic acids F3, FLP, and FSP is complementary to a different portion of the target nucleic acid molecule, in target nucleic acid molecule 3' to 5' order, as follows: F3, FLP, FSP;

(iii) FLP comprises, in a 3' to 5' order, a first portion (F2), complementary to a portion (F2c) of the target nucleic acid molecule, and a second portion (F1c), which is identical to a portion (F1c) of the target nucleic acid molecule 5' of F2c, but 3' of the portion (FSc) of the target nucleic acid to which FSP is complementary;

(iv) FSP comprises, in a 3' to 5' order, a first portion (FS) complementary to a portion (FSc) of the target nucleic acid molecule, and, optionally, a second portion (S1) that comprises a detectable nucleic acid sequence not complementary to the target nucleic acid;

(v) each of primer nucleic acids R3, RLP, and RSP is identical to a different portion of the target nucleic acid, as follows, in target nucleic acid molecule 5' to 3' order: R3, RLP, RSP;

(vi) RLP comprises, in a 3' to 5' order, a first portion (R2), identical to a portion (R2) of the target nucleic acid molecule, and a second portion (R1c), which is complementary to a portion (R1) of the target nucleic acid molecule 3' of R2, but upstream of the portion (RS) of the target nucleic acid identical to RSP; and (vii) RSP comprises, in a 3' to 5' order, a first portion identical to a portion (RS) of the target nucleic acid molecule 5' of FSc, and, optionally, a second portion (S2) that comprises a detectable nucleic acid sequence not complementary to the target nucleic acid, so that a nucleic acid detection product comprising, in 5' to 3' order, R1c, R2, R1, RS, FSc and (optionally) S1c is generated, wherein S1c is complementary to S1. In certain embodiments, the target nucleic acid molecule comprises a portion, D, which is 5' of FSc and 3' of RS, such that the nucleic acid detection product generated comprises, in a 5' to 3' order, R1c, R2, R1, RS, D, and (optionally) S1c. Generally, the nucleic acid product generated comprises only a single copy of D. In another aspect, the method further comprising detecting the presence and/or amount of the nucleic acid detection product. In certain embodiments, such a method comprises detecting the presence of D in the nucleic acid detection product.

In another embodiment, the method further comprises generating a nucleic acid detection product comprising, in 5' to 3' order, S1 (optional), FS, RSc, R2c, and R1. In certain embodiments, the target nucleic acid molecule comprises a portion, D, which is 5' of FSc and 3' of RS, such that the method further comprises generating a nucleic acid detection product generated comprising, in a 5' to 3' order, S1 (optional), FS, Dc, RSc, R2c, and R1, wherein Dc is complementary to D. Generally, such a nucleic acid product generated comprises only a single copy of Dc. In another aspect, the method further comprising detecting the presence and/or amount of the nucleic acid detection product. In certain embodiments, such a method comprises detecting the presence of Dc in the nucleic acid detection product.

In certain embodiments, methods are presented for generating a plurality (for example, two, three, four, five, six, seven, eight, or more) of different nucleic acid detection products from a plurality of different target nucleic acid molecules, wherein a separate set of nucleic acid primers (F3, FLP, FSP, R3, RLP, RSP) as described herein is utilized for each target nucleic acid molecule of interest. In certain embodiments, the plurality of nucleic acid detection products is generated in a single reaction vessel, e.g., tube or well. In other aspects, a plurality of different nucleic acid detection products is detected, e.g., detected in a single reaction vessel, for example, in a tube or well, e.g., in a closed tube format.

In such embodiments, primer nucleic acids FLP and RLP are amplification primers suitable for use in LAMP nucleic acid amplification reactions. Without wishing to be bound by any particular mechanism or theory, such methods comprise FLP and RLP mediated LAMP nucleic acid amplification reactions.

In such embodiments, primer nucleic acids FSP and RSP are examples of signal primers.

In such embodiments, primer nucleic acids F3 and R3 are examples of displacement primers.

In another embodiment, provided herein is a method for generating a nucleic acid extension product, comprising:

combining (i) a target nucleic acid molecule comprising a 3' and a 5' terminal hairpin structure, and (ii) a nucleic acid primer (FSP) comprising, in a 3' to 5' order, a first portion (FS) complementary to a portion (FSc) of the linear nucleic acid molecule 5' of the 3' hairpin structure and 3' of the 5' hairpin structure, and, optionally, a second portion (S1) that comprises a detectable nucleic acid sequence not complementary to the target nucleic acid molecule, under conditions that allow complementary nucleic acids to hybridize and nucleic acid extension reactions to occur, thereby hybridizing FSP to the target nucleic acid molecule, and extending FSP, so that a nucleic acid extension product comprising, in a 5' to 3' order, FSP and a nucleic acid sequence complementary to substantially all of the 5' terminal hairpin structure, is generated. In yet another embodiment, the nucleic acid extension product generated further comprises a 3' terminus that is complementary to substantially all of FSP.

As used herein, a 3' hairpin structure refers to a self-complementary hairpin structure that comprises the 3'-terminus of a nucleic acid molecule. Likewise, as used herein, a 5' hairpin structure refers to a self-complementary hairpin structure that comprise the 5' terminus of a nucleic acid molecule. Thus, a nucleic acid molecule that comprises a 5'- and a 3'-terminal hairpin structure contains self-complementary hairpin structures at each end of itself.

In certain embodiments, such a method can generate a plurality (for example, two, three, four, five, six, seven, eight, or more) of different nucleic acid extension products from a plurality of different target nucleic acid molecules, wherein a separate FSP is utilized for each target nucleic acid molecule of interest.

In another embodiment, provided herein is a method for generating a nucleic acid detection product, comprising:

combining (i) a target nucleic acid molecule comprising a 3' and a 5' terminal hairpin structure, (ii) a nucleic acid primer (FSP) comprising, in a 3' to 5' order, a first portion (FS) complementary to a portion (FSc) of the linear nucleic acid molecule 5' of the 3' hairpin structure and 3' of the 5' hairpin structure, and, optionally, a second portion (S1) that comprises a detectable nucleic acid sequence not complementary to the target nucleic acid molecule, and (iii) a nucleic acid primer (RLP) comprising, in a 3' to 5' order, a first portion (R2), identical to a loop portion of the 5' terminal hairpin structure, and a second portion (R1c), which is complementary to a portion (R1) of the target nucleic acid molecule 3' of R2, within the hairpin section of the 5' terminal hairpin structure, under conditions that allow complementary nucleic acids to hybridize and nucleic acid extension reactions to occur, so that a nucleic acid detection product comprising, in a 5' to 3' order, RLP (R1c and R2), R1, and a nucleic acid sequence complementary to substantially all of FSP, is generated. In another embodiment, the method further comprises generating a nucleic acid detection product comprising, in a 5' to 3' order, FSP (S1(optional) and FS), FS, RSc, R2c, and substantially all of R1, wherein RSc is complementary to RS, and R2c is complementary to R2. In another aspect, such methods can further comprise detecting the presence and/or amount of a nucleic acid detection product.

In certain embodiments, the target nucleic acid molecule comprises a portion, D, which is 5' of FSc and 3' of RS, such that the method comprises generating a nucleic acid detection product comprising, in a 5' to 3' order, RLP (R1c and R2), R1, D, and a nucleic acid sequence complementary to substantially all of FSP (S1(optional) and FS). In another aspect, the method further comprises detecting the presence and/or amount of the nucleic acid detection product. In another embodiment, such a method comprises detecting the presence of D in the nucleic acid detection product. In another embodiment, such a method can further comprise generating a nucleic acid detection product comprising, in a 5' to 3' order, FSP, Dc, RSc, R2c, and R1, wherein Dc is complementary to D. In another aspect, the method further comprising detecting the presence and/or amount of the nucleic acid detection product. In certain embodiments, such a method comprises detecting the presence of Dc in the nucleic acid detection product.

In certain embodiments, such methods can generate a plurality (for example, two, three, four, five, six, seven, eight, or more) of different nucleic acid detection products from a plurality of different target nucleic acid molecules, wherein a separate set of nucleic acid primers (FSP and RLP) as described herein is utilized for each target nucleic acid molecule of interest.

Also provided herein are kits for generation and detection of secondary LAMP products as presented herein, comprising (i) a nucleic acid signal primer, wherein at least a portion of the nucleic acid signal primer hybridizes to a region of a first target sequence, (ii) a nucleic acid amplification primer, wherein the amplification primer comprises a 3' terminal portion which hybridizes to a first target sequence region 3' of the target sequence region to which the signal primer hybridizes and a 5' terminal portion which comprises substantially the same nucleotide sequence as a region of the first target sequence 5' of the target sequence region to which the 3' terminal portion of the amplification primer hybridizes, and (iii) a displacement primer, which hybridizes to a region of the first target sequence 3' of the target sequence region to which the 3' terminal portion of the nucleic acid amplification primer hybridizes.

In a certain embodiment, any of the above-described kits further comprise (i) a second nucleic acid signal primer, wherein at least a portion of the second nucleic acid signal primer hybridizes to a region of a second target sequence, (ii) a second nucleic acid amplification primer, wherein the amplification primer comprises a 3' terminal portion which hybridizes to a second target sequence region 3' of the target sequence region to which the second signal primer hybridizes and a 5' terminal portion which comprises substantially the same nucleotide sequence as a region of the second target sequence 5' of the target sequence region to which the 3' terminal portion of the second amplification primer hybridizes, and (iii) a second displacement primer, which hybridizes to a region of the second target sequence 3' of the target sequence region to which the 3' terminal portion of the nucleic acid amplification primer hybridizes.

In another embodiment, any of the above-described kits further comprise (i) a third nucleic acid signal primer, wherein at least a portion of the nucleic acid signal primer hybridizes to a region of a third target sequence, (ii) a third nucleic acid amplification primer, wherein the amplification primer comprises a 3' terminal portion which hybridizes to a third target sequence region 3' of the target sequence region to which the third signal primer hybridizes and a 5' terminal portion which comprises substantially the same nucleotide sequence as a region of the third target sequence 5' of the target sequence region to which the 3' terminal portion of the third amplification primer hybridizes, and (iii) a third displacement primer, which hybridizes to a region of the third target sequence 3' of the target sequence region to which the 3' terminal portion of the nucleic acid amplification primer hybridizes. Further, contemplated herein are kits wherein 4, 5, 6, 7 or more target sequences are amplified and detected using the methods described herein.

In one embodiment, any of the above-described kits further comprise a hybridization probe. In one specific embodiment, the hybridization probe is a molecular beacon. In some embodiments, the signal primer in any of the above-described kits further comprises a reporter region. In one embodiment, such reporter group produces a fluorescent signal. In one specific embodiment, the reporter group is a fluorogenic hairpin. In one embodiment, the nucleic acid target sequence in any of the above-described kits is a sequence of *Mycobacterium tuberculosis*.

Applications for the methods, compositions, and kits presented herein include, for example, detection of microorganisms, diagnosis of diseases, e.g., infectious diseases, genetic disorders and genetic traits. For example, the methods and kits presented herein may be used in any biological or clinical application wherein the real-time detection of a particular nucleic acid or nucleic acids, e.g., gene, gene sequence, or gene mutation (e.g., a deletion, an insertion or a point mutation), RNA, e.g., mRNA or rRNA, in a biological sample is desirable. In one specific embodiment, the methods and kits presented herein, can be used to detect drug resistant tuberculosis via, e.g., detection of the presence of particular rpoB mutations of *Mycobacterium tuberculosis* in nucleic acid from a biological sample.

4. BRIEF DESCRIPTION OF THE DRAWINGS

FIG. 1 shows LAMP reaction with a signal primer (FSP), an amplification primer (FLP) and a displacement primer (F3), wherein the extension products P1, P2 and P3 are produced.

FIG. 8 shows a region of the *M. tuberculosis* katG gene (SEQ ID NO: 37). The nucleotides depicted correspond to nucleotides 771-1112 (numbered from the first coding nucleotide of the katG gene (locus tag "Rv1908c") of GenBank accession number NC_000962 Region: complement (2153889.2156111).

FIG. 9 shows a region of the *M. tuberculosis* inhA gene (SEQ ID NO: 38). The nucleotides depicted correspond to nucleotides 1673281-1673580 (non-coding nucleotides located in a regulatory region of the fabG1 (aka mabA) gene (locus tag "Rv1483"), which is part of an operon containing the inhA gene, of GenBank accession number NC_000962 Region: 1673440.1674183.

FIG. 10 shows a region of the *M. tuberculosis* gyrB gene (SEQ ID NO: 39). The nucleotides depicted correspond to nucleotides 412-720 (numbered from the first coding nucleotide of the gyrB gene (locus tag "Rv0005").

FIG. 11 shows use of a fluorophore/quencher pair linked to FLP-gyr and QP-gyr, respectively to detect the presence of a target sequence during the LAMP reaction.

5. DETAILED DESCRIPTION

5.1. Terminology

As used herein, the following terms and phrases are used as follows:

As used herein, the terms "about" and "approximately," unless otherwise indicated, refer to a value that is no more than 20% above or below the value being modified by the term.

A nucleic acid refers to a molecule composed of two or more monomeric nucleotides, and can include, for example, ribonucleic acids (RNAs), e.g., pre-mRNA, mRNA or rRNA molecules, deoxyribonucleic acids, e.g., cDNA or gDNA, single-stranded nucleic acids, double-stranded nucleic acids, or nucleic acids comprising deoxyribonucleotides, ribonucleotides, naturally occurring nucleotides, analogs of naturally occurring nucleotides, analogs of nucleotides, or a combination thereof. Nucleic acids can include, for example, peptide nucleic acids (PNAs).

A "nucleic acid primer," or "primer," refers to a nucleic acid molecule comprising a 3'-terminal —OH group that, upon hybridization to a complementary nucleic acid sequence, can be extended, e.g., via enzymatic nucleic acid replication. A nucleic acid primer generally comprises about 10-200, about 20-100, about 20-50, about 30-100, about 30-50, or about 20-30 nucleotides. Generally, at least 10 contiguous nucleotides of a primer are complementary to, e.g., fully complementary to, a target nucleic acid molecule.

A "signal primer," or "nucleic acid signal primer," is a nucleic acid primer comprising at least a first portion which is complementary to, and hybridizable to, a portion of a target nucleic acid molecule 5' to a portion of the target nucleic acid molecule to which an amplification primer (see below) is complementary and hybridizable. A signal primer optionally comprises a second portion, 5' to the first portion, that is not complementary to the target nucleic acid molecule. A signal primer comprises a 3'-OH group which can, for example, be extended, e.g., by DNA polymerase, when the signal primer is hybridized to a target sequence with the target sequence used as a template for the extension. Upon hybridization of the signal primer to the target nucleic acid molecule and extension of the hybridized signal primer, an extension product is produced an comprising a sequence complementary to the portion of the target nucleic acid used as a template during extension. A signal primer may further comprise one or more detectable moieties, e.g., one or more labeled reporter molecules, for example, fluorescent molecules. Exemplary signal primers, FSP and RSP, are depicted in the diagrams at FIGS. 1, 2B, 3B, and 4-6. When used in conjunction with one or more amplification primers, a signal primer or primers can be added to a reaction comprising a target nucleic acid molecule prior to, concurrently with, or after addition of the amplification primer(s).

An "amplification primer," or "nucleic acid amplification primer," is a nucleic acid primer suitable for amplification of a target nucleic acid molecule during a LAMP reaction. The LAMP reaction, in general, is described, e.g., in U.S. Pat. Nos. 6,974,670, 6,410,278 and in Notomi et al., Nucl. Acid Res. 28(12): e63 (2000) (hereinafter "Notomi et al."), which are hereby incorporated by reference in their entirety. An amplification primer comprises, in 3' to 5' order, a first portion, complementary to a portion of the target nucleic acid molecule, and a second portion, which is identical to a portion of the target nucleic acid molecule 5' of the portion to which the first portion of the amplification primer hybridizes, but is 3' of the nearest portion of the target nucleic acid molecule to which a signal primer hybridizes. An amplification primer comprises a 3'-OH group which, for example, is extendable by DNA polymerase when the first portion of the amplification primer is hybridized to the target sequence with the target sequence used as a template for the extension. Upon hybridization of the amplification primer to the target nucleic acid molecule and extension of the hybridized amplification primer, an extension product is produced comprising a sequence complementary to the portion of the target nucleic acid used as a template during extension. This extension product comprises the amplification primer and a nucleic acid sequence complementary to the second portion of the amplification primer positioned a sufficient number of nucleotides away from the amplification primer portion that a hairpin structure can be formed by hybridization of the nucleic acid sequence and the amplification primer portion of the extension product. As such, such an extension product comprises a hairpin sequence and is capable of forming a hairpin structure. Without wishing to be bound by any particular theory or mechanism, upon hybridization of an amplification primer and its nearest signal primer to a target nucleic acid molecule, the relative positions of the hybridized primers along the target nucleic acid molecule are such that extension of the hybridized amplification primer displaces the hybridized signal primer and its extension product from the target nucleic acid molecule. Exemplary amplification primers, FLP and RLP, are depicted in FIGS. 1-3 and 5.

Amplification products, amplified products or amplicons are copies of the target sequence generated by hybridization and extension of an amplification primer. These terms refer to either single stranded and double stranded amplification primer extension products which contain a copy of the original target sequence, including intermediates of the amplification reaction.

Secondary amplification products or secondary products are copies of the target sequence generated by hybridization and extension of a signal primer. A secondary amplification product or secondary product comprises an internal segment of the amplified target sequence. These terms also refer to either single stranded and double stranded extension products of signal primers, including intermediates in the process which generates the final double stranded form.

A "displacement primer" is a nucleic acid primer complementary to, and hybridizable to, a portion of a target nucleic acid molecule downstream of an amplification primer. One or more displacement primers can, for example, be used in conjunction with amplification primers for performing or initiating LAMP reactions. Without wishing to be bound by any particular theory or mechanism, upon hybridization of a displacement primer and its nearest amplification primer to a target nucleic acid molecule, the relative positions of the hybridized primers along the target nucleic acid molecule are such that extension of the hybridized displacement primer displaces the hybridized amplification primer and its extension product from the target nucleic acid molecule. Exemplary displacements primers, F3 and R3, are depicted at FIGS. 1-3.

Figure 2A:
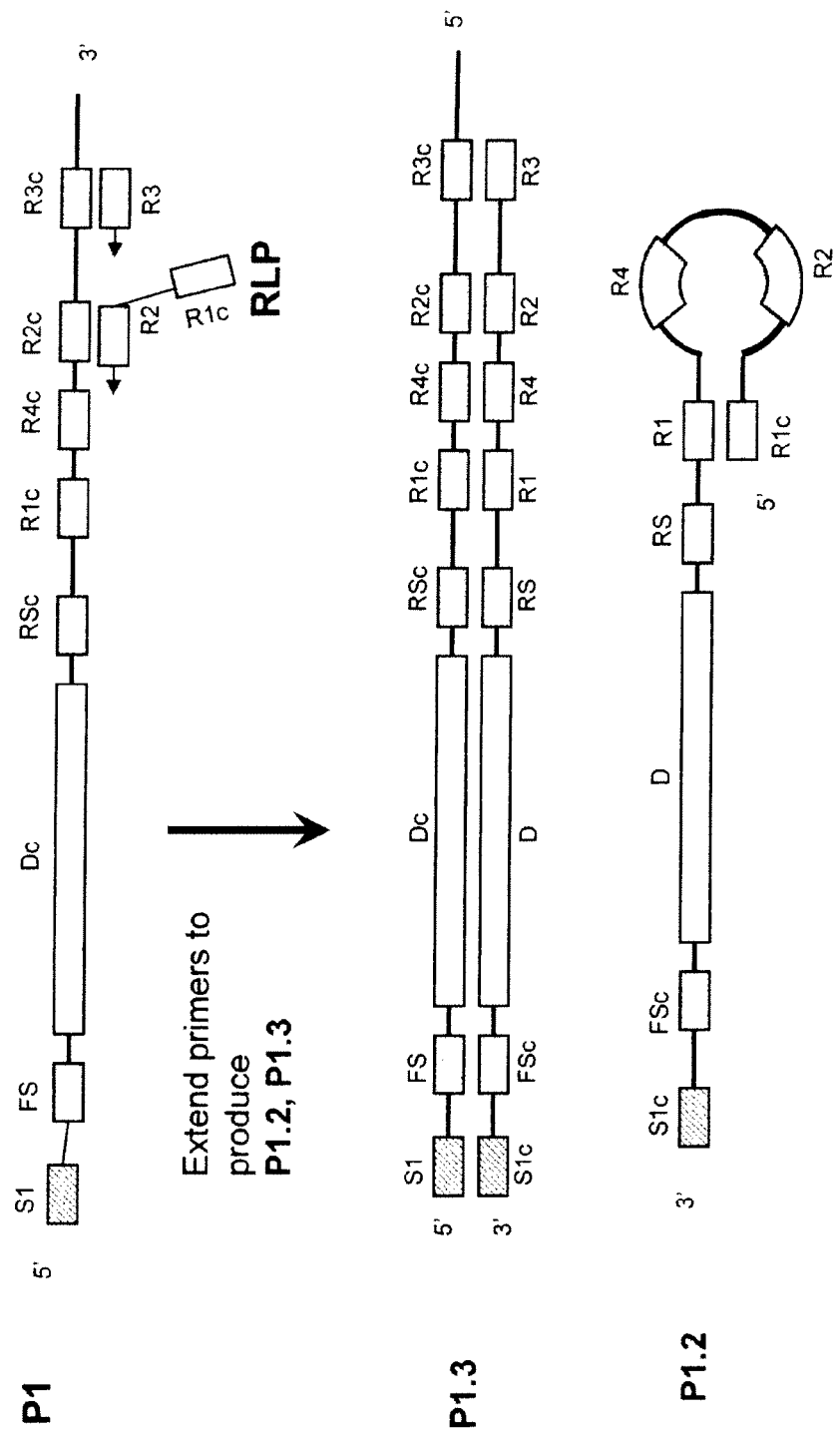
FIG. 2A shows LAMP reaction using P1 as a template with an amplification primer (RLP) and a displacement primer R3, wherein the extension products P1.2 and P1.3 are produced.

A "target nucleic acid molecule," can refer to any nucleic acid that can contains a nucleic acid of interest that can be detected via the methods described herein. For example, a target nucleic acid molecule can be used to generate a nucleic acid extension product and/or a nucleic acid detection product as described herein. In certain embodiments, a target nucleic acid molecule is a deoxyribonucleic acid (DNA). A target nucleic acid molecule can refer to the nucleic acid taken from a sample, or can refer to nucleic acids derived from the original nucleic acid obtained from a sample, e.g., nucleic acids produced by one or more rounds of replicating, amplifying, e.g., via isothermal amplification, for example, one or more LAMP reactions, and/or reverse transcribing of the original nucleic acid obtained from the sample. A target nucleic acid molecule can comprise a portion, D, or its complement, Dc, of particular interest for one or more detection applications. Unless otherwise noted, the terms "target nucleic acid molecule," "target nucleic acid," "target nucleic acid sequence," and "target sequence" are used interchangeably herein.

A target nucleic acid molecule can be present, for example, in a biological sample. A biological sample can include, for example, animal, plant or microbial tissues, cells, cultures and excretions, or extracts therefrom. Such microbial samples, can include, but are not limited to biological samples such as bacterial, viral or mycoplasma samples, and can, for example, comprise genomic DNA, RNA, mRNA, rRNA and the like. A biological sample can be from a subject sample or patient sample, such as, for example, a bronchoalveolar lavage, bronchial wash, a pharyngeal exudate, a tracheal aspirate, a blood sample, a serum sample, a plasma sample, a bone sample, a skin sample, a soft tissue sample, an intestinal tract specimen, a genital tract specimen, breast milk, a lymph sample, cerebrospinal fluid, pleural fluid, a sputum sample, a urine sample, a nasal secretion, tears, a bile sample, an ascites fluid sample, pus, synovial fluid, vitreous fluid, a vaginal secretion, semen, and urethral samples. In some embodiments, two, three or more samples are obtained from a subject. In specific embodiments, two or more samples are obtained from two or more tissues, organs and/or secretions from a subject.

A "nucleic acid detection product," as used herein, is a nucleic acid molecule comprising a target nucleic acid molecule portion of interest, or a complement thereof, wherein the nucleic acid detection product does not comprise a hairpin nucleic acid sequence or structure. For example, a nucleic acid detection product can comprise a target nucleic acid molecule portion, D, or its complement, Dc, of particular importance in one or more detection applications. Generally, a nucleic acid detection product will not comprise the entire target nucleic acid molecule. Nucleic acid detection products will generally comprise all or substantially all of a signal primer, or complement thereof.

Two nucleic acids are "complementary to" each other when a sufficient number of nucleobases of one nucleic acid can hydrogen bond with the corresponding nucleobases of the second nucleic acid such that pairing ("base pairing," generally Watson-Crick base pairing) between the two nucleic acids can occur. "Complementarity", as used herein, refers to the capacity for pairing between nucleotides of a first nucleic acid and a second nucleic acid. Non-complementary nucleobases between two nucleic acids may be tolerated provided that the two nucleic acids remain able to specifically hybridize to each other. Moreover, a first nucleic acid may hybridize over one or more segments of a second nucleic acid such that intervening or adjacent segments are not involved in the hybridization event. In certain embodiments, a first nucleic acid, e.g., a nucleic acid primer, or a specified portion thereof, is at least, 70%, 80%, 85%, 86%, 87%, 88%, 89%, 90%, 91%, 92%, 93%, 94%, 95%, 96%, 97%, 98%, 99%, or 100% complementary to a second nucleic acid, e.g., a target nucleic acid molecule, or specified portion thereof.

In certain embodiments, a primer, or a specified portion thereof, is fully complementary (i.e., 100% complementary) to a target nucleic acid, or specified portion thereof. As used herein, "fully complementary" means each nucleobase of one nucleic acid is capable of precise base pairing with the corresponding nucleobases of a second nucleic acid. For example, a 20 nucleobase primer is fully complementary to a target sequence that is 400 nucleobases long, so long as there is a corresponding 20 nucleobase portion of the target nucleic acid that is fully complementary to the primer. Fully complementary can also be used in reference to a specified portion of the first and/or the second nucleic acid. For example, a 20 nucleobase portion of a 30 nucleobase primer can be "fully complementary" to a target sequence that is 400 nucleobases long. The 20 nucleobase portion of the 30 nucleobase primer is fully complementary to the target sequence if the target sequence has a corresponding 20 nucleobase portion wherein each nucleobase is complementary to the 20 nucleobase portion of the primer. At the same time, the entire 30 nucleobase antisense compound may or may not be fully complementary to the target sequence, depending on whether the remaining 10 nucleobases of the primer are also complementary to the target sequence. The location of a non-complementary nucleobase or nucleobases may be at the 5' end or 3' end of the nucleic acid, e.g., the primer. Alternatively, the non-complementary nucleobase or nucleobases may be at an internal position of the nucleic acid, e.g., the primer. When two or more non-complementary nucleobases are present, they may be contiguous (i.e., linked) or non-contiguous.

As used herein, "portion" refers to a defined number of contiguous (i.e. linked) nucleobases within a target nucleic acid molecule or primer. A portion of a nucleic acid sequence can refer to any fraction of the whole sequence, but will generally refer, at a minimum, to a length of the sequence that can hybridize to a complementary nucleic acid sequence, e.g., at least 5-8 nucleobases.

Percent complementarity of two nucleic acids can be determined using routine methods. For example, a nucleic acid primer in which 18 of 20 nucleobases of the primer are complementary to a portion of a target nucleic acid molecule, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, a primer which is 18 nucleobases in length having 2 (two) noncomplementary nucleobases which are flanked by two portions of complete complementarity with the target nucleic acid would have 90% overall complementarity with the target nucleic acid. Percent complementarity of these two nucleic acids can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

"Hybridization" refers to the annealing of complementary nucleic acid molecules. When two nucleic acids "hybridize to" each other, or when one nucleic acid "hybridizes to" another, the two nucleic acid molecules exhibit a sufficient number of complementary nucleobases that the two nucleic acid molecules can anneal to each other under the particular conditions (e.g., temperature, salt and other buffer conditions) being utilized for a particular reaction. The most common mechanism of hybridization involves hydrogen bonding (e.g., Watson-Crick, Hoogsteen or reversed Hoogsteen hydrogen bonding) between complementary nucleobases of the nucleic acid molecules. Hybridization can occur under varying conditions. Stringent conditions are sequence-dependent and are determined by the nature and composition of the nucleic acid molecules to be hybridized. Nucleic acid hybridization techniques and conditions are known to the skilled artisan and have been described extensively. See, e.g., Sambrook et al., Molecular Cloning: A Laboratory Manual $2^{nd}$ ed., Cold Spring Harbor Press, 1989; Ausubel et al., 1987, *Current Protocols in Molecular Biology*; Greene Publishing and Wiley-Interscience, New York; Tijessen, 1993, *Hybridization with Nucleic Acid Probes*, Elsevier Science Publishers, B. V.; and Kricka, 1992, *Non-Isotopic DNA Probe Techniques*, Academic Press, San Diego, Calif.

As used herein, when two nucleic acid sequences are referred to as being "identical" to each other if the first nucleic acid sequence is sufficiently complementary to the complementary sequence of the second nucleic acid sequence that these two sequences (i.e., the first nucleic acid sequence and the complement of the second nucleic acid sequence) would specifically hybridize with each other. In certain embodiments, two identical nucleic acid sequences or specified portions thereof, are 100% identical, that is, share an exact nucleobase match with each other.

5.2. Methods for Generation of Nucleic Acid Detection and Secondary Lamp Products Although generally performed in conjunction with LAMP isothermal nucleic acid amplification, the methods presented herein allow for the generation of nucleic acid detection products that lack the problematic concatenated secondary structures (e.g., stem-loop DNAs with several inverted repeats of the target nucleic acid molecule and cauliflower-like structures with multiple loops formed by annealing between alternatively inverted repeats of the target molecule in the same strand, each with high melting-temperatures and strong tendencies to fold back on themselves) present in nucleic acids produced using conventional LAMP. For example, in one aspect, presented herein are methods and compositions that allow real-time, sequence-specific, generation and detection of one or more nucleic acid sequence within one or more target nucleic acid molecules by utilizing signal primers or primer pairs in conjunction with a LAMP reaction to generate a nucleic acid detection products comprising target nucleic acid molecule portions of interest, or complements thereof, wherein the nucleic acid detection products do not comprise a hairpin nucleic acid sequence or structure, thereby making the nucleic acid detection products particularly amenable to detection. For example, the nucleic acid detection product or products can be detected by conventional hybridization of reporter probes or by incorporating a reporter group into one or more signal primers used to generate the nucleic acid detection product(s). In addition, the nucleic acid detection products can, for example, be produced in real-time, in conjunction with, e.g., during, the LAMP process, and provide the option of detecting multiple nucleic acid detection products within a single reaction vessel, e.g., tube, using, for example, a real-time fluorescence format.

In one embodiment, presented herein is a method for generating a nucleic acid detection product, comprising, combining a target nucleic acid molecule and displacement primer nucleic acids F3 and R3, amplification primers FLP and RLP, and signal primers FSP and RSP, under conditions that allow complementary nucleic acids to hybridize and nucleic acid extension reactions to occur, (i) the target nucleic acid and each of the primer nucleic acids comprises a 5' terminus ("5'") and a 3' terminus ("3'");

(ii) each of the primer nucleic acids F3, FLP, and FSP is complementary to a different portion of the target nucleic acid molecule, in target nucleic acid molecule 3' to 5' order, as follows: F3, FLP, FSP;

(iii) FLP comprises, in a 3' to 5' order, a first portion (F2), complementary to a portion (F2c) of the target nucleic acid molecule, and a second portion (F1c), which is identical to a portion (F1) of the target nucleic acid molecule 5' of F2c, but 3' of the portion (FSc) of the target nucleic acid to which FSP is complementary;

(iv) FSP comprises, in a 3' to 5' order, a first portion (FS) complementary to a portion (FSc) of the target nucleic acid molecule, and, optionally, a second portion (S1) that comprises a detectable nucleic acid sequence not complementary to the target nucleic acid;

(v) each of primer nucleic acids R3, RLP, and RSP is identical to a different portion of the target nucleic acid, as follows, in target nucleic acid molecule 5' to 3' order: R3, RLP, RSP;

(vi) RLP comprises, in a 3' to 5' order, a first portion (R2), identical to a portion (R2) of the target nucleic acid molecule, and a second portion (R1c), which is complementary to a portion (R1) of the target nucleic acid molecule 3' of R2, but 5' of the portion (RS) of the target nucleic acid identical to RSP; and (vii) RSP comprises, in a 3' to 5' order, a first portion identical to a portion (RS) of the target nucleic acid molecule 5' of FSc, and, optionally, a second portion (S2) that comprises a detectable nucleic acid sequence not complementary to the target nucleic acid, so that a nucleic acid detection product comprising, in 5' to 3' order, R1c, R2, R1, RS, FSc and (optionally) S1c is generated. In certain embodiments, the target nucleic acid molecule comprises a portion, D, which is 5' of FSc and 3' of RS, such that the nucleic acid detection product generated comprises, in a 5' to 3' order, R1c, R2, R1, RS, D, and (optionally) S1c. In another aspect, the method further comprising detecting the presence and/or amount of the nucleic acid detection product. In certain embodiments, such a method comprises detecting the presence of D in the nucleic acid detection product.

In another embodiment, the method further comprises generating a nucleic acid detection product comprising, in 5' to 3' order, S1, FS, RSc, R2c, and R1. In certain embodiments, the target nucleic acid molecule comprises a portion, D, which is 5' of FSc and 3' of RS, such that the method further comprises generating a nucleic acid detection product generated comprising, in a 5' to 3' order, S1, FS, Dc, RSc, R2c, and R1, wherein Dc is complementary to D. In another aspect, the method further comprising detecting the presence and/or amount of the nucleic acid detection product. In certain embodiments, such a method comprises detecting the presence of Dc in the nucleic acid detection product.

In certain embodiments, methods are presented for generating a plurality (for example, two, three, four, five, six, seven, eight, or more) of different nucleic acid detection products from a plurality of different target nucleic acid molecules, wherein a separate set of nucleic acid primers (F3, FLP, FSP, R3, RLP, RSP) as described herein is utilized for each target nucleic acid molecule of interest. In certain embodiments, the plurality of nucleic acid detection products is generated in a single reaction vessel, e.g., tube or well. In other aspects, a plurality of different nucleic acid detection products is detected, e.g., detected in a single reaction vessel, for example, in a tube or well, e.g., in a closed tube format.

In such embodiments, primer nucleic acids FLP and RLP are amplification primers suitable for use in LAMP nucleic acid amplification reactions. Without wishing to be bound by any particular mechanism or theory, such methods comprise FLP and RLP mediated LAMP nucleic acid amplification reactions.

In such embodiments, primer nucleic acids FSP and RSP are examples of signal primers.

In such embodiments, primer nucleic acids F3 and R3 are examples of displacement primers.

While, in the above embodiments, a signal primer pair was used, the methods provided herein also allow for use of single signal primer in such reactions.

In such embodiments, the signal primer or primers can be combined concurrently with the displacement primers and amplification primers. Alternatively, the signal primer or primers can be combined at a separate time, e.g., either prior to or subsequent to, the displacement primers. For example, in certain embodiments, one or more signal primers can be added about 1 minute, 2 minutes, 3 minutes, 4 minutes, 5 minutes, 1-5 minutes, 5-10 minutes, 10-15 minutes, 15-20 minutes, 20-25 minutes, 25-30 minutes, 30-60 minutes, or 1-2 hours after the amplification primers and the displacement primers, e.g., after initiation of the hybridization and extension reactions.

Reaction conditions for the methods described herein will vary somewhat, e.g., depending upon the particular target nucleic acid molecule and primer molecule sequences and hybridizing lengths, and the particular extension product reaction chosen, but such conditions would be well known to those of skill in the art, and can routinely be chosen. In general, the conditions suitable for the methods described herein are conditions that would be suitable for performing conventional LAMP reactions. See, e.g., U.S. Pat. Nos. 6,974, 670 (see, especially, cols. 4-7), and 6,410,278, and Notomi et al., each of which is incorporated herein by reference in its entirety.

Also provided herein are methods for detecting amplification products of LAMP reactions by real-time primer extension. In one embodiment, identification of a target sequence by LAMP is detected by simultaneously generating a secondary amplification product, the production of which is tightly coupled to amplification of the target sequence. In certain embodiments, this secondary amplification product is produced during the LAMP reaction without requiring any additional amplification steps or manipulations. In one embodiment, once generated, the secondary amplification product does not interfere with or inhibit normal LAMP of the desired target sequence. The methods of the present are therefore useful for real-time monitoring of LAMP and detecting amplification of the target sequence, especially in situations where real-time detection of multiple target sequences or sequence variants within a single-tube format is desirable.

In certain aspects, amplification primers for LAMP are hybridized to a target sequence and the target sequence is amplified generally as described by U.S. Pat. Nos. 6,974,670, 6,410,278 and Notomi et al., hereby incorporated by reference in their entirety. As described in these references, the LAMP method amplifies DNA with high specificity, efficiency and rapidity under isothermal conditions by employing a DNA polymerase and a set of four specially designed primers that recognize a total of six distinct sequences on the target DNA. As described in Notomi et al., during the LAMP reaction, an inner primer ("an amplification primer") containing sequences of the sense and antisense strands of the target DNA initiates LAMP. See, Notomi et al. Then, strand displacement DNA synthesis primed by an outer primer ("displacement primer") releases a single-stranded DNA. Id. This serves as template for DNA synthesis primed by the second amplification and displacement primers that hybridize to the other end of the target, which produces a dumb-bell shaped stem-loop DNA structure. Id. This stem-loop DNA then serves as the starting material for LAMP cycling. Id. In subsequent LAMP cycling, one amplification primer hybridizes to the loop on the product and initiates displacement DNA synthesis, yielding the original stem-loop DNA and a new stem-loop DNA. Id. The cycling reaction continues with accumulation of $10^9$ copies of target in less than an hour. Id. The final products are stem-loop DNAs with several inverted repeats of the target and cauliflower-like structures with multiple loops formed by annealing between alternately inverted repeats of the target in the same strand. As a result, LAMP produces a high molecular weight DNA consisting of numerous copies of the original target sequence (and compliments) concatenated into self-complementary hairpin structures, which, because of their high melting temperatures and strong tendency to fold back on themselves, are not amenable to detection by routine probe-based hybridization methods. Further, the steps of the LAMP reaction are described in detail in, for example, U.S. Pat. No. 6,974,670, columns 4-7, the disclosure of which is incorporated herein by reference in its entirety.

However, provided herein is the LAMP reaction which further comprises at least one signal primer which results in simultaneous or concurrent generation of a secondary amplification product for use in detecting, monitoring or localizing amplification products produced by the LAMP reaction. In some embodiments, the secondary amplification products may also contain features which facilitate their detection, capture or immobilization.

The secondary amplification products are produced in the LAMP reactions described herein by inclusion of at least one signal primer in the reaction mixture. In some embodiments, it may be preferable to include two signal primers that hybridize to sites located between the priming sites of the forward and reverse LAMP amplification primers. In yet other embodiments, three, four, five, six, seven, eight or more signal primers are used, wherein such signal primers can simultaneously detect two, three, four or more target sequences or sequence variants.

In certain aspects of the present methods, the signal primer or signal primers hybridize to the target sequence downstream of the hybridization site of the amplification primers. In one embodiment, such primers are extended by polymerase in a manner similar to extension of the amplification primers. The signal primer hybridizes at a site in the target sequence such that extension of the amplification primer displaces the extension product of the signal primer. In one embodiment, the 3' end of the signal primer comprises a sequence which hybridizes to the target sequence. In certain embodiments, the entire signal primer may hybridize to the target sequence, for example when it is unmodified or chemically modified for detection by addition of a reporter group, label or affinity ligand. In other embodiments, the 5' end of the signal primer may comprise a sequence which does not hybridize to the target sequence but which contains special nucleotide sequences (often involving structural features) which facilitate detection or capture of the secondary amplification product). In some embodiments, such chemical modifications and special sequences are incorporated into the secondary amplification products when the signal primers are hybridized and extended on a template.

In one embodiment, the template for the reaction is the nucleic acid having complementary nucleotide sequences linked in a single-stranded chain. A single-stranded chain is a strand not separated into two or more molecules upon dissociation of base pairing. In another embodiment, a nucleic acid which serves as a template in the reaction contains a nucleotide sequence for forming a loop between the complementary sequences in a chain or chains. In one embodiment, the complementary nucleotide sequence of the template can form base pairing or can anneal in the same chain. In some embodiments, the template nucleic acid comprises a loop/hairpin sequence wherein there is no base pairing at a bent hinged portion.

The term complementary as used herein in the context of two nucleic acid sequences does not require complete complementarity, but merely sufficient complementarity to allow the two nucleic acids to anneal under the conditions used.

The primers utilized herein, generally comprise nucleic acids that provide an —OH group at the 3'-terminus that, upon hybridization to a complementary nucleic acid sequence can be extended, e.g., via enzymatic nucleic acid replication in, for example, nucleic acid amplification reactions. In certain embodiments, the primer is an oligonucleotide comprises sufficient nucleotide length as to be capable of base pairing with a complementary chain and to maintain necessary specificity under the given environment in the various reactions of synthesizing nucleic acid. In some embodiments, a primer comprises about 5 to 200 nucleotides, more preferably about 10 to 50 nucleotides. In one embodiment, the methods described herein employ signal primers which do not function as amplification primers in the LAMP reaction. Any extension products formed through errant extension of such signal primers on non-target templates will not undergo subsequent amplification. In certain embodiments, signal primers may be added to the amplification reaction prior to initiation of amplification with no apparent increase in background signal levels. This can greatly simplifies the detection procedure and makes possible homogeneous real-time analysis of LAMP reactions.

A target nucleic acid sequence may, for example, be contained in or obtained from a biological sample. A biological sample can include, for example, animal, plant or microbial tissues, cells, cultures and excretions, or extracts therefrom. Such microbial samples, can include, but are not limited to biological samples such as bacterial, viral or mycoplasma samples, and can, for example, comprise genomic DNA, RNA, mRNA, rRNA and the like.

In certain embodiments, nucleic acid is amplified by a single enzyme under isothermal conditions. In a specific embodiment, the methods herein can utilize a polymerase catalyzing strand displacement-type synthesis of complementary chain.

In certain embodiments, the methods described herein are conducted in the absence of temperature cycling. In embodiments wherein the nucleic acid to be used as a template is double-stranded, the nucleic acid may, at least initially, undergo heat denaturation, to allow for primer annealing.

The methods described herein can allow for detection of more than one target, for example, concurrent or multiplexed detection, in a sequence-specific manner. In some embodiments, detection of two, three, four, five, six or more target sequences or sequence variants is performed.

The present methods include, in one aspect, methods for generating a nucleic acid signal extension product and amplification in a loop-mediated isothermal amplification reaction, comprising:

(a) hybridizing a first nucleic acid signal primer, a first nucleic acid amplification primer, and a first nucleic acid displacement primer to regions of a nucleic acid target sequence;

wherein at least a portion of the first nucleic acid signal primer hybridizes to a target sequence region downstream of the target sequence region to which the 3' terminal portion of the first nucleic acid amplification primer hybridizes;

wherein the first nucleic acid amplification primer comprises i) a 3' terminal portion that hybridizes to a target sequence region upstream of the target sequence region to which the first signal primer hybridizes, and ii) a 5' terminal portion that comprises substantially the same nucleotide sequence as a region of the target sequence downstream of the target sequence region to which the 3' terminal portion of the first nucleic acid amplification primer hybridizes; and wherein the first nucleic acid displacement primer hybridizes to a target sequence region upstream of the target sequence region to which the 3' terminal portion of the first nucleic acid amplification primer hybridizes;

(b) extending the hybridized first nucleic acid signal primer on the nucleic acid target sequence to produce a first signal extension product; extending the hybridized first nucleic acid amplification primer on the nucleic acid target sequence such that extension of the first amplification primer displaces the first signal extension product from the nucleic acid target sequence; and extending the first nucleic acid displacement primer, such that extension of the first nucleic acid displacement primer displaces a first amplification extension product from the nucleic acid target sequence.

As used herein, the term "downstream" refers to the direction or region toward which an extension product extends from the primer being referred to, e.g., as in (a), above, the first nucleic acid amplification primer. As used herein, the term "upstream" to the region or direction away, or opposite, from the direction or region toward which an extension product extends from the primer being referred to, e.g., as in (a), above, the first signal primer.

In some embodiments, the above-described method further comprises:

(a) hybridizing a second nucleic acid signal primer, a second nucleic acid amplification primer, and a second nucleic acid displacement primer to regions of the first signal extension product;

wherein at least a portion of the second nucleic acid signal primer hybridizes to a first signal extension product region downstream of the first signal extension product region to which the 3' terminal portion of the second nucleic acid amplification primer hybridizes;

wherein the second nucleic acid amplification primer comprises i) a 3' terminal portion that hybridizes to a first signal extension product region upstream of the first signal extension product region to which the second signal primer hybridizes, and ii) a 5' terminal portion that comprises substantially the same nucleotide sequence as a region of the first signal extension product downstream of the first signal extension product region to which the 3' terminal portion of the second nucleic acid amplification primer hybridizes; and wherein the second nucleic acid displacement primer hybridizes to a first signal extension product region upstream of the first signal extension product region to which the 3' terminal portion of the second nucleic acid amplification primer hybridizes;

(b) extending the hybridized second nucleic acid signal primer on the first signal extension product to produce a second signal extension product; extending the hybridized second nucleic acid amplification primer on the first signal extension product such that extension of the second amplification primer displaces the second signal extension product from the first signal extension product; and extending the second nucleic acid displacement primer, such that extension of the second nucleic acid displacement primer displaces a second amplification extension product from the first signal extension product.

Further provided herein are methods for generating a nucleic acid signal extension product and amplification in a loop-mediated isothermal amplification reaction, comprising:

(a) hybridizing a second nucleic acid signal primer, a second nucleic acid amplification primer, and a second nucleic acid displacement primer to regions of a first signal extension product;

wherein at least a portion of the second nucleic acid signal primer hybridizes to a first signal extension product region downstream of the first signal extension product region to which the 3' terminal portion of the second nucleic acid amplification primer hybridizes;

wherein the second nucleic acid amplification primer comprises i) a 3' terminal portion that hybridizes to a first signal extension product region upstream of the first signal extension product region to which the second signal primer hybridizes, and ii) a 5' terminal portion that comprises substantially the same nucleotide sequence as a region of the first signal extension product downstream of the first signal extension product region to which the 3' terminal portion of the second nucleic acid amplification primer hybridizes;

wherein the second nucleic acid displacement primer hybridizes to a first signal extension product region upstream of the first signal extension product region to which the 3' terminal portion of the second nucleic acid amplification primer hybridizes;

and wherein the first signal extension product is generated concurrently with an amplification in a loop-mediated isothermal amplification reaction;

(b) extending the hybridized second nucleic acid signal primer on the first signal extension product to produce a second signal extension product; extending the hybridized second nucleic acid amplification primer on the first signal extension product such that extension of the second amplification primer displaces the second signal extension product from the first signal extension product; and extending the second nucleic acid displacement primer, such that extension of the second nucleic acid displacement primer displaces a second amplification extension product from the first signal extension product.

In one embodiment, presented herein is a method for generating a nucleic acid signal extension product during a loop-mediated isothermal amplification reaction, comprising:

(a) hybridizing a nucleic acid signal primer to a region of the nucleic acid target sequence, wherein said target sequence comprises at least one self-complementary hairpin structure generated during a loop-mediated isothermal amplification reaction, and wherein said region is not situated in a loop region of the hairpin structure; and (b) extending the hybridized nucleic acid signal primer on the nucleic acid target sequence to produce a first signal extension product, wherein said first signal extension product comprises one hairpin structure.

The above-described method, may, for example, further comprise detecting the first signal extension product. In one embodiment, the signal primer comprises a hybridization region and a reporter region, wherein the hybridization region hybridizes to the region of the nucleic acid target sequence, and wherein the reporter region produces a fluorescent signal. In another embodiment, the signal primer lacks a reporter group.

In another embodiment, methods are provided for generating nucleic acid signal extension products during a loop-mediated isothermal amplification reaction, comprising:

(a) hybridizing a nucleic acid signal primer to a nucleic acid target sequence region, wherein the target sequence comprises at least one self-complementary hairpin structure generated during a loop-mediated isothermal amplification reaction;

(b) extending the hybridized nucleic acid signal primer on the nucleic acid target sequence to produce a first signal extension product, wherein said first signal extension product comprises a hairpin structure;

(c) hybridizing a nucleic acid amplification primer to a loop region of the first signal extension product, and extending the hybridized nucleic acid amplification primer on the first signal extension product to produce a second signal extension product and a third signal extension product, wherein the second signal extension product lacks a hairpin structure; and wherein the third signal has a hairpin structure on its 5' end;

The above-described method may further comprise detecting the second and/or the third signal extension product.

In yet another embodiment, presented herein is a method for generating nucleic acid signal extension products during a loop-mediated isothermal amplification reaction, comprising:

(a) hybridizing a nucleic acid signal primer to a nucleic acid target sequence region, wherein the target sequence comprises at least one self-complementary hairpin structure generated during a loop-mediated isothermal amplification reaction;

(b) extending the hybridized nucleic acid signal primer on the nucleic acid target sequence to produce a first signal extension product, wherein said first signal extension product comprises a hairpin structure;

(c) hybridizing a nucleic acid amplification primer to a loop region of the first signal extension product, and extending the hybridized nucleic acid amplification primer on the first signal extension product to produce a second signal extension product and a third signal extension product, wherein the second signal extension product lacks a hairpin structure; and wherein the third signal extension product is single-stranded and has a hairpin structure on its 5' end;

(d) hybridizing the nucleic acid signal primer to the third signal extension product, and extending the hybridized nucleic acid signal primer on the third signal extension product to produce a fourth signal extension product, wherein the fourth signal extension product comprises double-stranded nucleic acid.

In one embodiment, the above-described method further comprises detecting the fourth signal extension product.

In certain embodiments, two or more target sequences or sequence variants are detected concurrently, wherein two or more nucleic acid signal primers which hybridize to said two or more target sequences are used. In one embodiment, the two or more target sequences are present in the same contiguous nucleotide sequence or on two different nucleotide sequences. In another embodiment, the two or more target sequences or sequence variants are derived from one organism or from two or more different organisms. In some embodiments, the first, second, third, or fourth signal extension product is detected in real-time. In certain embodiments, the first, second, third, or fourth signal extension product is detected in a closed tube format. In other embodiments, the first, second, third, or fourth signal extension product is detected post-amplification.

In one embodiment, the first, second, third, or fourth signal extension product is detected by a hybridization probe. In one such embodiment, the hybridization probe is a single nucleotide difference sensitive probe. In another embodiment, hybridization probe is fluorogenic. In a specific embodiment, the hybridization probe is a molecular beacon. In another specific embodiment, the first, second, third, or fourth signal extension product is detected using a fluorogenic probe or Surface-enhanced Raman scattering (SERS)-labeled probe.

In certain embodiments, the signal primer comprises a hybridization region and a reporter region, wherein the hybridization region hybridizes to the region of the nucleic acid target sequence, and wherein the first, second, third, or fourth signal extension product is detected by means of the reporter region. In one embodiment, the reporter group produces a fluorescent signal. In another embodiment, the reporter group is a fluorogenic hairpin. In another embodiment, the signal primer lacks a reporter group. In yet another embodiment, the first, the second, the third, or the fourth signal extension product is detected by means of a modification to facilitate capture of the signal product incorporated into one of the signal primers. The methods herein described may be used to detect, for example, drug resistant TB.

In one embodiment, a signal primer or primers are added after initiation of the LAMP reaction. For example, a signal primer or primers may be added 1 minute, 2 minutes, 3 minutes, 4 minutes, 5 minutes, 1-5 minutes, 5-10 minutes. 10-15 minutes, 15-20 minutes, 20-25 minutes, 25-30 minutes, or 30-60 minutes, or more than 1 hour after the initiation of the LAMP reaction.

In yet another embodiment, a signal primer is added to the LAMP reaction simultaneously with the addition of an amplification primer/s and/or displacement primer/s, or simultaneously with the initiation of the LAMP reaction.

The present methods can also include a method for concurrently generating signal extension products and an amplification in a loop-mediated isothermal amplification reaction, comprising:

(a) hybridizing a first signal primer to a first strand of a target sequence;

(b) hybridizing a first amplification primer to the first strand of the target sequence upstream of the first signal primer, wherein the first amplification primer comprises a 3' terminal portion which hybridizes to the first strand of the target sequence and a 5' terminal portion comprising substantially the same nucleotide sequence as an arbitrary region of the first strand of the target sequence;

(c) extending the hybridized first signal primer on the first strand of the target sequence to produce a first signal extension product and extending the hybridized first amplification primer on the first strand of the target sequence such that extension of the first amplification primer displaces the first signal extension product from the target sequence;

(d) hybridizing a first displacement primer to the first strand of the target sequence upstream of the first amplification primer, and extending the first displacement primer from its 3' end to displace the first amplification extension product from the target sequence;

(e) hybridizing a second signal primer to the displaced first signal extension product;

(f) hybridizing a second amplification primer to the first signal extension product upstream of the second signal primer, wherein the second amplification primer comprises a 3' terminal portion which hybridizes to the first signal extension product and a 5' terminal portion comprising substantially the same nucleotide sequence as an arbitrary region of the first signal extension product;

(g) extending the hybridized second signal primer on the first signal extension product to produce a second signal extension product and extending the hybridized second amplification primer on the first signal extension product such that extension of the second amplification primer displaces the second signal extension product from the first signal extension product; and (h) hybridizing a second displacement primer to the first signal extension product upstream of the second amplification primer, and extending the second displacement primer from its 3' end to displace the second amplification extension product from the first signal extension product.

In one embodiment of such methods, the first signal extension product and the second signal extension product lack self-complementary hairpin structures. In another embodiment of such methods, a 5' terminal portion of the first signal primer does not comprise substantially the same nucleotide sequence as an arbitrary region of the first strand of the target sequence; and a 5' terminal portion of the second signal primer does not comprise substantially the same nucleotide sequence as an arbitrary region of the first signal extension product.

In certain embodiments, the method further comprises hybridizing the first signal primer to the displaced second signal extension product and extending the hybridized first signal primer on the second signal extension product such that a double-stranded signal product is generated.

In one embodiment, the method further comprises:

(a) hybridizing the second signal primer to a second strand of the target sequence;

(b) hybridizing the second amplification primer to the second strand of the target sequence upstream of the second signal primer, wherein the second amplification primer comprises a 3' terminal portion which hybridizes to the second strand of the target sequence and a 5' terminal portion comprising substantially the same nucleotide sequence as an arbitrary region of the second strand of the target sequence;

(c) extending the hybridized second signal primer on the second strand of the target sequence to produce a third signal extension product and extending the hybridized second amplification primer on the second strand of the target sequence such that extension of the second amplification primer displaces the third signal extension product from the target sequence;

(d) hybridizing a second displacement primer to the second strand of the target sequence upstream of the second amplification primer, and extending the second displacement primer from its 3' end to displace the third amplification extension product from the target sequence;

(e) hybridizing the first signal primer to the displaced third signal extension product;

(f) hybridizing the first amplification primer to the third signal extension product upstream of the first signal primer, wherein the first amplification primer comprises a 3' terminal portion which hybridizes to the third signal extension product and a 5' terminal portion comprising substantially the same nucleotide sequence as an arbitrary region of the third signal extension product;

(g) extending the hybridized first signal primer on the third signal extension product to produce a fourth signal extension product and extending the hybridized first amplification primer on the third signal extension product such that extension of the first amplification primer displaces the fourth signal extension product from the third signal extension product; and (h) hybridizing the first displacement primer to the third signal extension product upstream of the first amplification primer, and extending the first displacement primer from its 3' end to displace the fourth amplification extension product from the third signal extension product.

These methods may, for example, further comprise hybridizing the second signal primer to the displaced fourth signal extension product and extending the hybridized second signal primer on the fourth signal extension product such that a double-stranded signal product is generated.

In certain embodiments, two or more target sequences or sequence variants are used concurrently, and signal products and amplification products are generated for each of said target sequences or sequence variants. In such embodiments, the signal extension products of two or more targets or sequence variants may be detected. In some embodiment, the signal extension products are detected by probe-based hybridization methods. In a specific embodiment, the signal extension products are detected by molecular beacons.

In certain embodiments, the signal products are detected in real-time. In other embodiments, the signal products are detected post-amplification. In a specific embodiments, the methods described herein may be used to detect drug resistant TB.

Some embodiments of the above-described methods further comprise detecting the signal products by means of a chemical modification or special nucleotide sequence incorporated into one or more of the signal primers. In one embodiment, the signal products are detected by means of a reporter group incorporated into one of the signal primers. In a specific embodiment, the reporter group is a fluorogenic hairpin. In another embodiment, the signal primer lacks a reporter group. In yet other embodiments, the method further comprises detecting the signal products by means of a modification to facilitate capture of the signal product incorporated into one of the signal primers.

In one embodiment, the signal primers do not function as amplification primers in the LAMP reaction in which they are employed. In such embodiments, this feature may allow the signal primers to be added to the amplification reaction mixture without promoting the high levels of background signal generated by other primer-based methods. High levels of background signal are believed to be due to non-specific priming and subsequent amplification of spuriously primed non-target DNA when the primers are capable of functioning as amplification primers.

FIGS. 1, 2A, 2B, 3A, 3B, 4, 5, 6 and 7 illustrate certain embodiments of the methods presented herein, for example, embodiments in which a pair of signal primers is used for detecting amplification of a target sequence. Without wishing to be limited to any particular mechanism or theory, it is believed that the displacement, amplification and signal primers may simultaneously hybridize to a target sequence in the presented target generation scheme, such that extension of each upstream primer displaces the extension product of the downstream primer and simultaneously generates amplifiable target fragments and secondary amplification products.

FIG. 1 illustrates an embodiment wherein a signal primer FSP is included in the LAMP reaction mixture and hybridizes to the target sequence downstream (as used herein and as illustrated in this figure, this term refers to the direction or region toward which an extension product extends from the primer being referred to, in this case, the first amplification primer) of a first amplification primer by hybridization of the FS portion of the signal primer to the FSc region of the target sequence. The S1 portion of the FSP signal primer sequence depicted includes a reporter group or label, or is a structural feature to facilitate detection or capture. S1 may or may not hybridize, but is shown here as not hybridizing to clarify the different functional features of the signal primer. For the purposes of this illustration, S1 will contain a reporter group, but may contain other chemical modifications or structural features. In some embodiments, signal primers utilized herein lack S1 and/or S2 regions depicted in FIGS. 1-6. FLP is a LAMP amplification primer which hybridizes to the target sequence upstream (as used herein and illustrated by this figure, this term refers to the region or direction away, or opposite, from the direction or region toward which an extension product extends from the primer being referred to, in this case, the signal primer) of the signal primer. FLP contains the F2 portion and the F1c portion, wherein the F2 portion hybridizes to the target sequence, and wherein F1c portion is complementary to a region of the newly synthesized strand such that it forms a loop structure upon displacement of the amplification primer extension product from the target sequence (see structure P2). Both amplification primer FLP and signal primer FSP are extended by DNA polymerase using the target sequence as a template. The signal primer extension product P1 is displaced from the template by extension of amplification primer FLP. The amplification primer extension product P2 is in turn displaced from the template by extension of a displacement primer F3, yielding P2 and P3 products. The F1c region of the amplification primer extension product hybridizes to the F1 region in the same strand thus forming a loop-shaped structure on its 5'-terminal. The signal primer extension product P1 is a product uniquely generated using the methods described herein.

FIG. 2A illustrates an embodiment wherein a second LAMP amplification primer (RLP) and a second displacement primer (R3) hybridize to signal extension product P1 (produced in the amplification process depicted in FIG. 1). The R2 portion of RLP hybridizes to the R2c region of P1, and it is extended by DNA polymerase using the first signal extension product as a template. The second amplification primer extension products are displaced from the template by a second displacement primer R3 producing products P1.2 and P1.3. The R1c region of the P1.2 product hybridizes to the R1 region in the same strand thus forming a loop-shaped structure on its 5'-terminal.

Figure 2B:
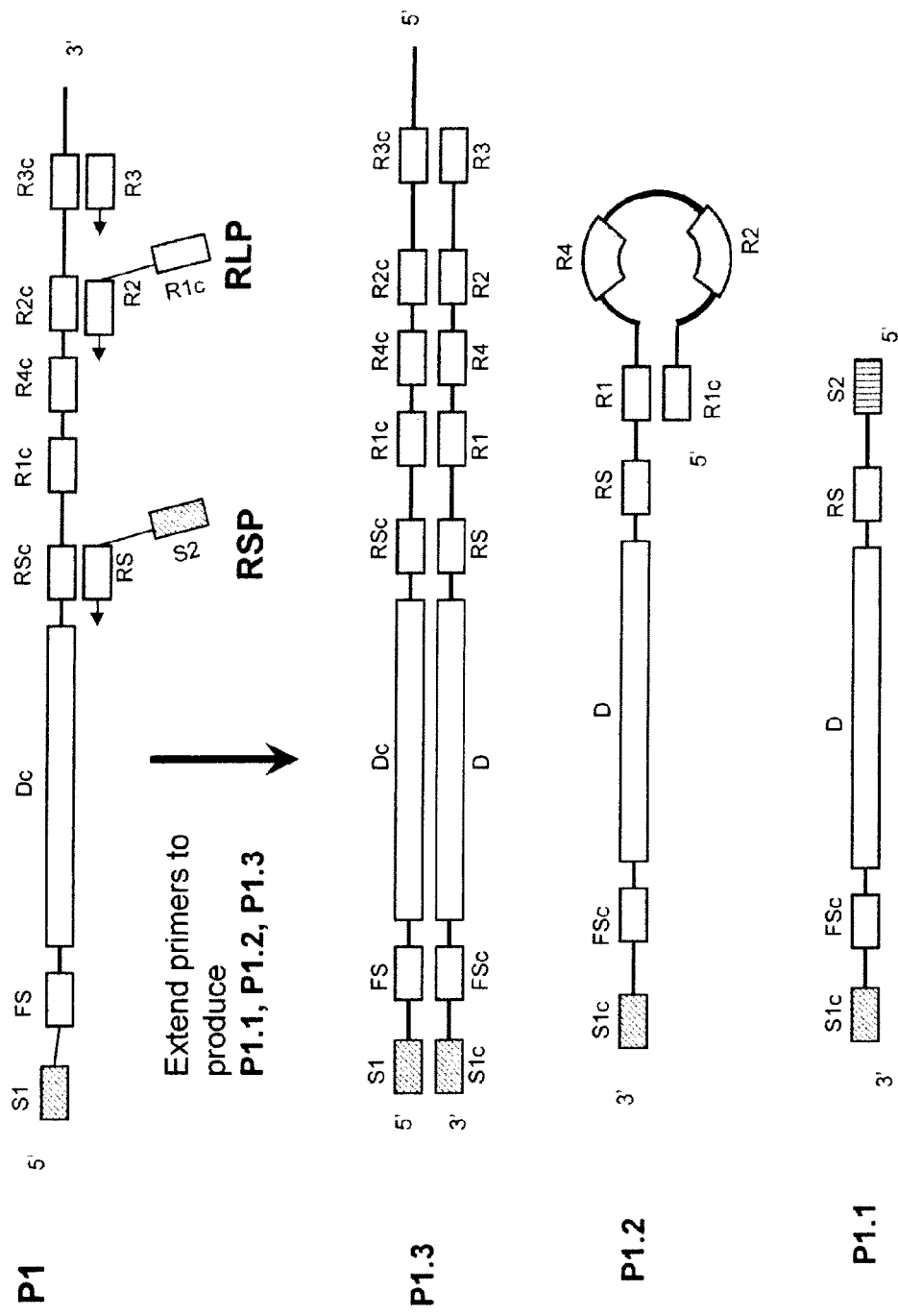
FIG. 2B shows LAMP reaction using P1 as a template with a signal primer (RSP), an amplification primer (FLP) and a displacement primer (F3), wherein the extension products P1.1, P1.2 and P1.3 are produced.

FIG. 2B illustrates an embodiment wherein a second signal primer (RSP), a second LAMP amplification primer (RLP) and a second displacement primer (R3) hybridize to signal extension product P1 (produced in the amplification process depicted in FIG. 1). The RS portion of RSP hybridizes to the RSc region of P1 target sequence downstream of a second amplification primer. The S2 portion of the RSP signal primer sequence includes a reporter group or label, or is a structural feature to facilitate detection or capture. S2 may or may not hybridize to P1 (in FIG. 2B, S2 does not hybridize to P1). RLP is a second LAMP amplification primer which hybridizes to the target sequence upstream of the signal primer. RLP contains the R2 portion and the R1c portion, wherein the R2 portion hybridizes to the target sequence, and wherein R1c portion is complementary to a region of the newly synthesized strand such that it forms a loop structure upon displacement of the amplification primer extension product from the target sequence (see structure P2). The products are extended by DNA polymerase. The signal primer extension product P1.1 is displaced from the template P1 by extension of amplification primer RLP. The amplification primer extension product P1.2 is in turn displaced from the template by extension of a displacement primer R3, yielding P1.2 and P1.3 products. The R1c region of the amplification primer extension product P1.2 hybridizes to the R1 region in the same strand thus forming a loop-shaped structure on its 5'-terminal. A key feature of P1.1 is its lack of hairpin structures that would impede detection of target sequences by means of fluorogenic hybridization probes such as molecular beacons. As a result of this lack of hairpins, a mutation (e.g., a single nucleotide difference or SNP) or a sequence variation in such secondary LAMP product can be detected by molecular beacons or other probe (e.g., SNP sensitive probe).

Figure 3A:
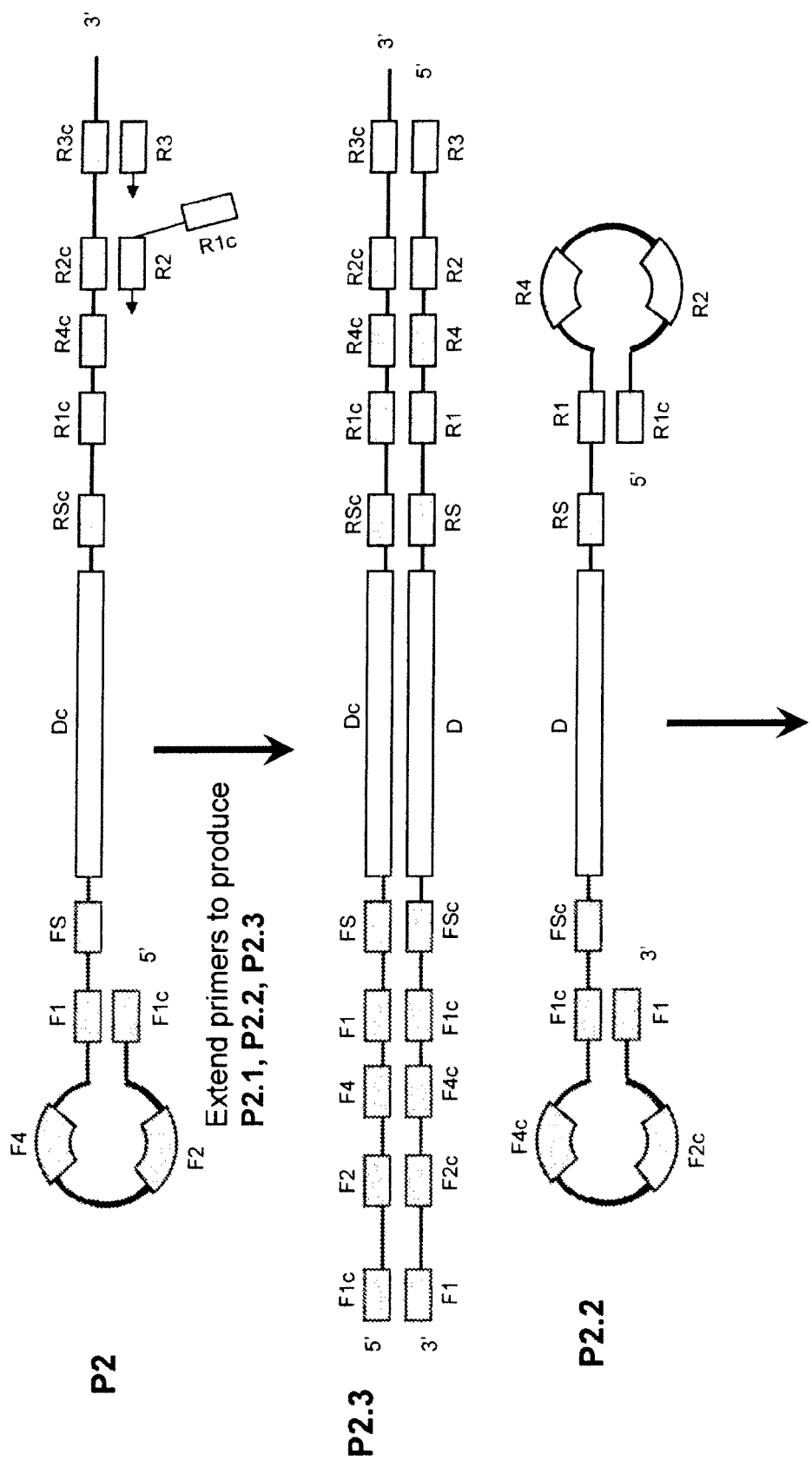
FIG. 3A shows LAMP reaction using P2 as a template with an amplification primer (RLP) and a displacement primer (R3), wherein the extension products P2.2 and P2.3 are produced.

FIG. 3A illustrates an embodiment wherein a second LAMP amplification primer (RLP) and a second displacement primer (R3) hybridize to amplification extension product P2 (produced in the amplification process depicted in FIG. 1). The R2 portion of RLP hybridizes to the R2c region of P2, and it is extended by DNA polymerase. The second amplification primer extension products are displaced from its template by a second displacement primer R3 producing products P2.2 and P2.3. The R1c region of the P2.2 product hybridizes to the R1 region in the same strand, thus forming a loop-shaped structure on its 5'-terminal. Because P2 template contains a loop structure on its 5'-terminal, the resulting P2.2 product features loops on both 5'- and 3'-terminals, producing a dumb-bell-shaped structure.

Figure 3B:
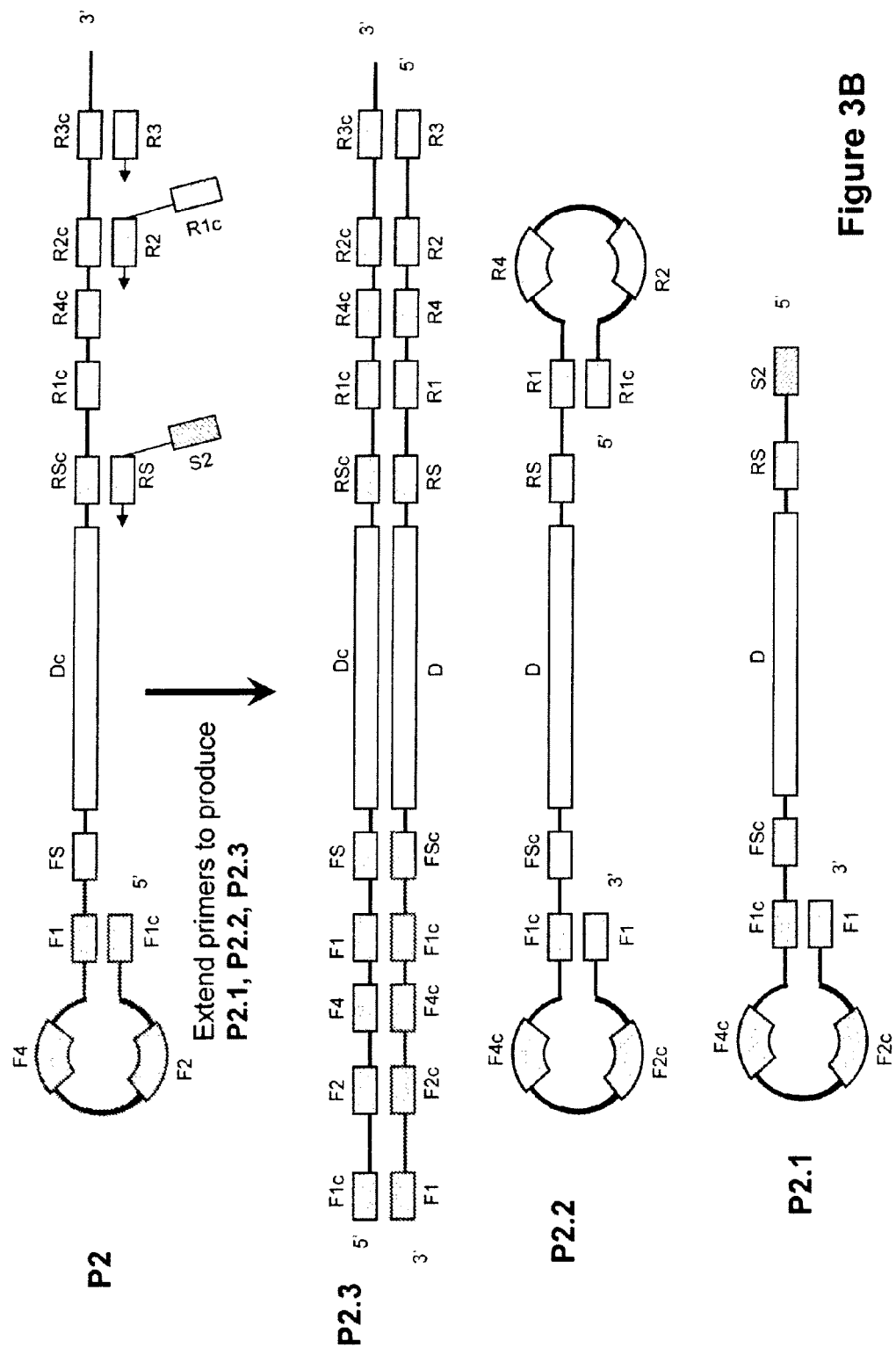
FIG. 3B shows LAMP reaction using P2 as a template with a signal primer (RSP), an amplification primer (RLP) and a displacement primer (R3), wherein the extension products P2.2 and P2.3 are produced.

FIG. 3B illustrates an embodiment wherein a second signal primer (RSP), a second LAMP amplification primer (RLP) and a second displacement primer (R3) hybridize to signal extension product P2 (produced in the amplification process depicted in FIG. 1). The RS portion of RSP hybridizes to the RSc region of P1 target sequence downstream of a second amplification primer. The S2 portion of the RSP signal primer sequence includes a reporter group or label, or is a structural feature to facilitate detection or capture. S2 may or may not hybridize to P2 (in FIG. 3B, S2 does not hybridize to P2). RLP is a second LAMP amplification primer which hybridizes to the target sequence upstream of the signal primer. RLP contains the R2 portion and the R1c portion, wherein the R2 portion hybridizes to the target sequence, and wherein R1c portion is complementary to a region of the newly synthesized strand such that it forms a loop structure upon displacement of the amplification primer extension product from the target sequence (see structure P2.2). The products are extended by DNA polymerase. The signal primer extension product P2.1 is displaced from the template P2 by extension of amplification primer RLP. The amplification primer extension product P2.2 is in turn displaced from the template by extension of a displacement primer R3, yielding P2.2 and P2.3 products. The R1c region of the amplification primer extension product P2.2 hybridizes to the R1 region in the same strand thus forming a loop-shaped structure on its 5'-terminal. Because P2 template contains a loop structure on its 5'-terminal, the resulting P2.2 product features loops on both 5'- and 3'-terminals, producing a dumb-bell-shaped structure.

Figure 4:
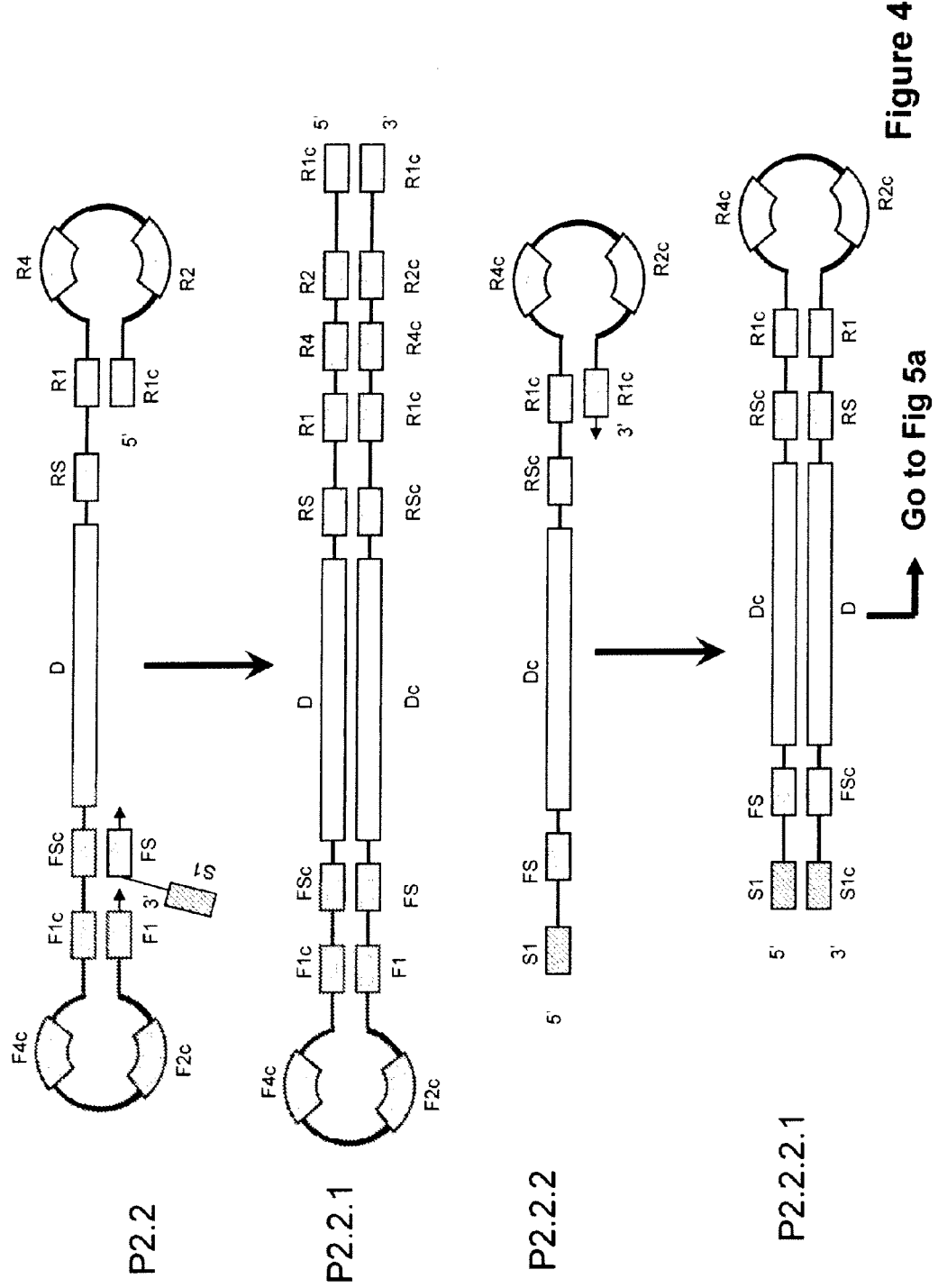
FIG. 4 shows an amplification reaction using LAMP-generated P2.2 product as a template with a signal primer (FSP), wherein the extension products P2.2.1, P2.2.2 and P2.2.2.1 are produced.

FIG. 4 illustrates an embodiment wherein a first signal primer (FSP) hybridizes to extension product P2.2 (produced in the amplification process depicted in FIGS. 3A and 3B), wherein P2.2 contains dumb-bell loop structures on its 5' and 3'-terminal ends generated during a LAMP reaction. The FS portion of FSP primer hybridizes to the FSc portion of P2.2, and it is extended by DNA polymerase. The extension product is displaced by internal 5' to 3' extension as illustrated in FIG. 4 to produce P2.2.1 and P.2.2.2, wherein P.2.2.1 product is double-stranded and P2.2.2 signal extension product contains a loop on its 3'-terminal end and may be extended by DNA polymerase to form a double-stranded product P.2.2.2.1.

Figure 5:
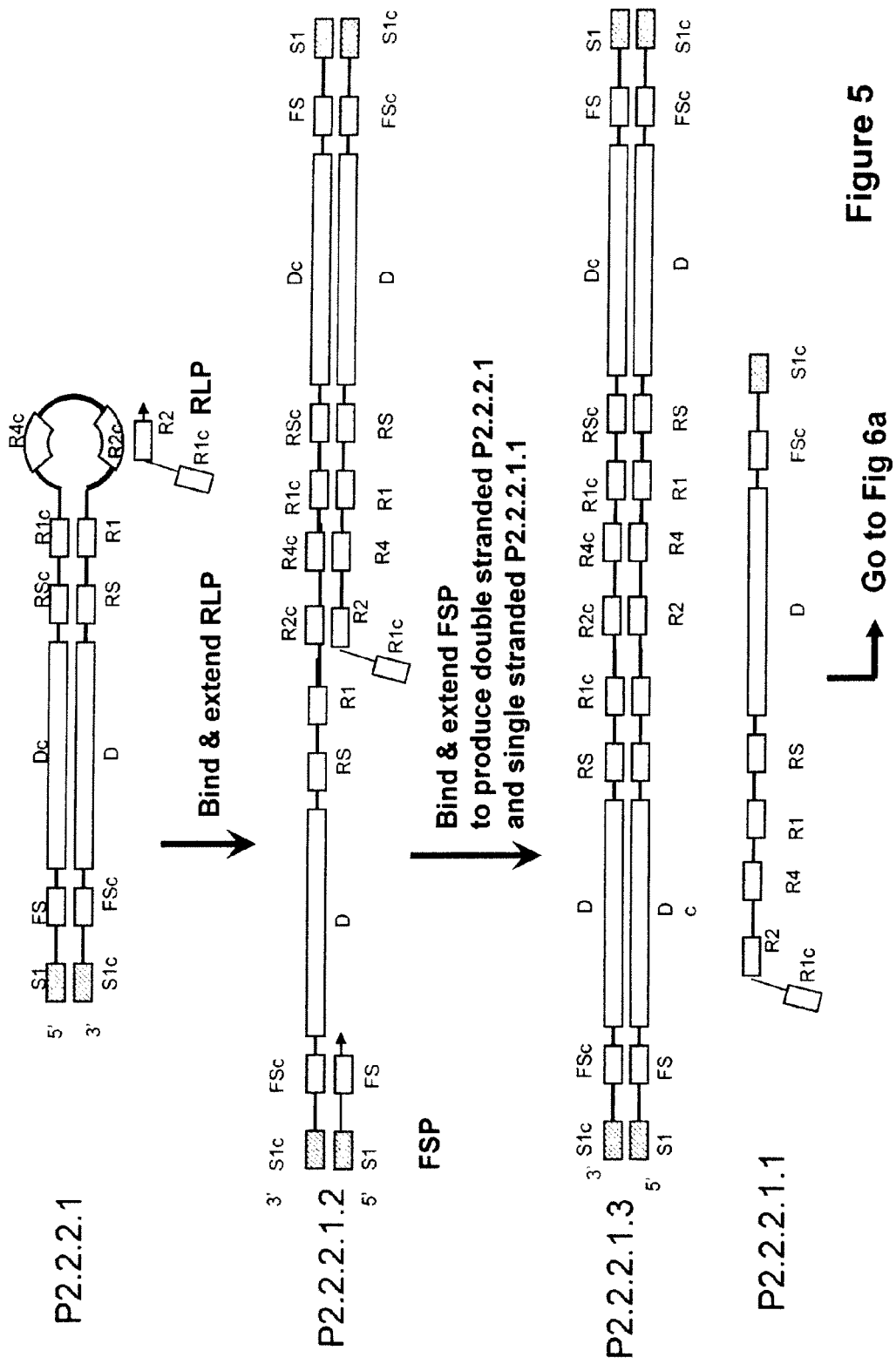
FIG. 5 shows an amplification reaction using LAMP-generated P2.2.2.1 product as a template with an amplification primer (RLP) and a signal primer (FSP), wherein the extension products P2.2.2.1.2, P2.2.2.1.3 and P2.2.2.1.1 are produced.

FIG. 5 illustrates an embodiment wherein a second amplification primer (RLP) hybridizes to extension product P2.2.2.1 (produced in the amplification process depicted in FIG. 4), wherein RLP hybridizes to the sequence inside the loop region of P.22.2.1, the region which does not form base pairing with an opposing strand. The R2 portion of RLP primer hybridizes to the R2c portion in the loop of P.2.2.2.1, and it is extended by DNA polymerase to generate P.2.2.2.1.2, wherein such extension opens up the loop region of P.2.2.2.1 to form P.2.2.2.1.2. Further, a first signal primer (FSP) hybridizes to P.2.2.2.1.2, wherein the FS portion of FSP hybridizes to FSc and the S1 portion hybridizes to S1c, and is extended by DNA polymerase, wherein such extension displaces extension product P.2.2.2.1.1 from P.2.2.2.1.2 and also produces a double-stranded product P.2.2.2.1.3. P.2.2.2.1.1 is single-stranded.

Figure 6:
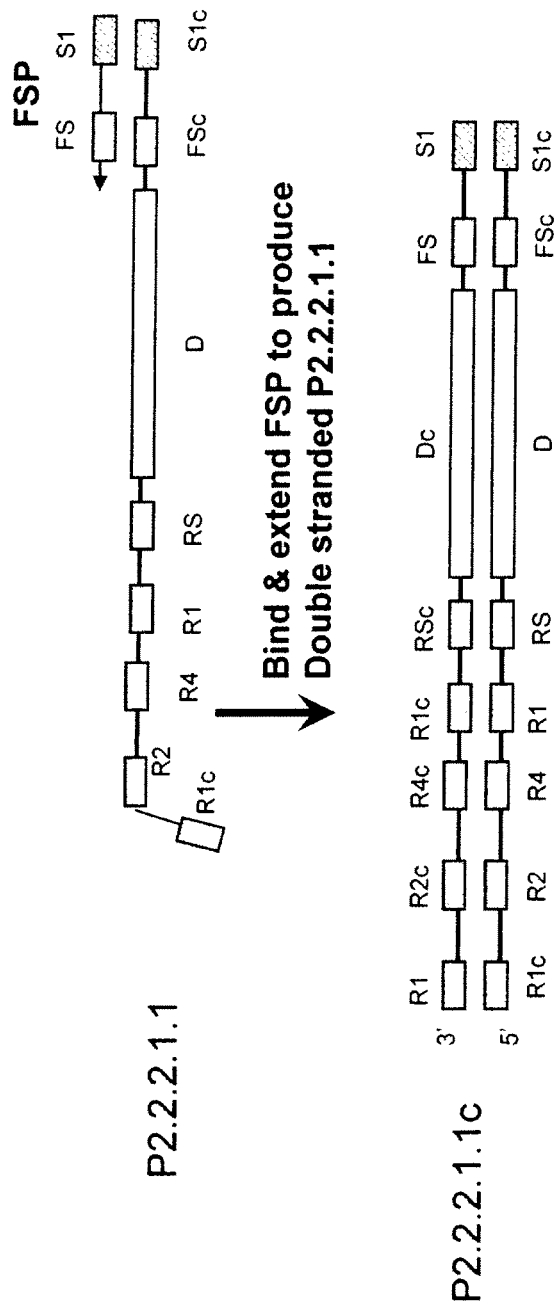
FIG. 6 shows an amplification reaction using P2.2.2.1 product as a template with a signal primer (FSP), wherein the extension product P2.2.2.1.1c is produced.

FIG. 6 illustrates an embodiment wherein a first signal primer (FSP) hybridizes to extension product P.2.2.2.1.1 and is extended by DNA polymerase to produce double-stranded product P.2.2.2.1.1c.

In one embodiment, a signal primer or primers (e.g., FSP and/or RSP depicted in FIGS. 1-6), is added after initiation of a LAMP reaction, for example, after 1 minute, 2 minutes, 3 minutes, 4 minutes, 5 minutes, 1-5 minutes, 5-10 minutes. 10-15 minutes, 15-20 minutes, 20-25 minutes, 25-30 minutes, or 30-60 minutes, or more than 1 hour after the initiation of the LAMP reaction. In some embodiments, a signal primer/s and a LAMP amplification primer/s are not added to the amplification reaction simultaneously. In one such embodiment, signal extension products depicted in FIGS. 1, 2B and 3B are not generated because, at the time of addition of a signal primer/s, all DNA in the LAMP reaction is converted either into double-stranded products such as P3 (see FIG. 1) or into products such as P2.2 (see FIG. 4). In another such embodiments, signal extension products of the type depicted in FIGS. 4, 5 and 6 are generated. In some such embodiments, all signal extension products generated have at least one structure substantially similar or identical to that of one of P.2.2.1, P.2.2.2or P.2.2.2.1(as depicted in FIG. 4), or that of P.2.2.2.1.2or P.2.2.2.1.3or P.2.2.2.1.1. (as depicted in FIG. 5), or that of P.2.2.2.1.c (as depicted in FIG. 6). In other such embodiments, the methods do not generate signal extension products such as P1 (depicted in FIG. 1), P1.1 (FIG. 2B) or P2.1 (depicted in FIG. 3B).

FIGS. 1-6 are presented for illustrative purposes only, and do not show all of molecular species produced during the LAMP reaction, nor do these figures show the variety of secondary products formed when secondary primers, such as FSP and RSP, are included in the LAMP reaction. Likewise, FIGS. 1-6 only exemplify some of the products of the LAMP reaction and some of the secondary products produced during the LAMP reaction of the methods. Further, extension products of the amplification reactions presented such as, for example, P1.1, will be produced through many pathways involving various intermediaries during a LAMP reaction.

The methods present herein further contemplate use of loop primers in the LAMP amplification reaction such as loop primers. See, e.g., Nagamine et al. (Mol. and Cell. Probes 16, 223-229 (2002)). Such loop primers generally hybridize to the stem-loops of the LAMP amplification reaction products, but do not hybridize to loops to which amplification primers hybridize. Use of such loop primers can, for example, substantially reduce LAMP reaction times. In such embodiments, the present methods can, for example, additionally contain a loop primer or primers. For example, the methods can utilize one or two loop primers for amplification of one target sequence or, e.g., can utilize three, four, five, six or more loop primers depending on the number of the target sequences to be amplified and/or detected. Such loop primers may hybridize, for example, to the single-stranded loop in P2 between regions F2 and F1 in FIG. 1, 3A or 3B; or to the loop in P1.2 between regions R2 and R1 in FIG. 2A or 2B; or to the loop in P2.2 in FIG. 3A or 4.

The present methods can, for example, comprise generation and/or detection of secondary LAMP signal extension products in less than 10 minutes, less than 15 minutes, less than 20 minutes, less than 30 minutes, less than 45 minutes, less than 50 minutes, less than 60 minutes, or less than in 1.5 hours or less than 2 hours, or less than 3 hours.

5.3. Methods for Detection of Nucleic Acid Detection and Secondary Lamp Products A key feature of the nucleic acid detection products and secondary LAMP products described herein is the absence of hairpin, potential hairpin structure, or hairpin sequences capable of forming a hairpin structure, which would hinder detection of customary LAMP products via conventional techniques such as molecular beacons. As such, any technique known to the skilled artisan for detecting a nucleic acid sequence, e.g., via probe or other sequence hybridization can routinely be used to detect the nucleic acid detection products and secondary LAMP products described herein. Presented below are exemplary, non-limiting examples of techniques that can routinely be used for such detection.

In one embodiment, specific target sequences contained within sequence D of the secondary products generated as described above and illustrated in FIGS. 1-6 may be detected by hybridization probes. A hybridization probe may be any nucleic acid that hybridizes to a target nucleic acid sequence and facilitates its detection. Generally, a hybridization probe is a fragment of nucleic acid of variable length (e.g., from about 10, 25, 50 or 100 bases, and up to about 200, 300, 400, 500, 600, 700, 800, 900, 1000, 1200, 1500 or 2000 bases long), which is used to detect in nucleic acid samples the presence of nucleotide sequences (the DNA target) that are complementary to the sequence in the probe. In some embodiments, the probe works by hybridizing to single-stranded nucleic acid whose base sequence allows probe-target base pairing due to complementarity between the probe and the target. In certain embodiments, to detect hybridization of the probe to its target sequence, the probe is tagged or labeled with a detectable marker. A detectable marker may, for example, be a radioactive isotope, an antibody-based marker, a fluorescence-based marker, or any other marker. In one embodiment, the molecular marker is non-radioactive. In another embodiment, the probe is labeled with a fluorescent label. In a specific embodiment, target detection methods using hybridization probes employ fluorescence quenching technology. In some embodiments, the labeled probe is first denatured (by heating or under alkaline conditions) into single DNA strands and then hybridized to the target nucleic acid. In a specific embodiment, the molecular marker used is suited for monitoring the synthesis of specific nucleic acids in real time.

In one embodiment, specific target sequences may be detected using an oligonucleotide containing the donor fluorophore and the acceptor fluorophore such that there is a detectable difference in the fluorescence properties of one or both when the oligonucleotide is non-hybridized vs. when it is hybridized to its complementary sequence. In this format, donor fluorescence is typically increased and energy transfer/ quenching are decreased when the oligonucleotide is hybridized. For example, a self-complementary oligonucleotide labeled at each end may form a hairpin which brings the two fluorophores (e.g., the 5' and 3' ends) into close proximity where energy transfer and quenching can occur. Hybridization of the self-complementary oligonucleotide to its complement on a second oligonucleotide disrupts the hairpin and increases the distance between the two dyes, thus reducing quenching. Such hairpin structure is known to be very stable such that conversion to the unquenched, hybridized form is often slow and only moderately favored.

In a specific embodiment, specific target sequences may be detected using molecular beacon/s. Molecular beacons are nucleic acid probes that undergo a spontaneous fluorogenic conformational change when they hybridize to their targets. Tyagi and Kramer, "Molecular Beacons: Probes that Fluoresce upon Hybridization," *Nature Biotechnology* 14, 303-308 (1996), incorporated herein by reference in its entirety. Molecular beacons are hairpin shaped molecules with an internally quenched fluorophore whose fluorescence is restored when they bind to a target nucleic acid sequence. Specifically, a molecular beacon is a hairpin containing a detector sequence in the loop between the self-complementary arms of the hairpin which form the stem. The base-paired stem must melt in order for the detector sequence to hybridize to the target and cause a reduction in quenching. Molecular beacons are particularly suited for monitoring the synthesis of specific nucleic acids in real time. Id. When used in nucleic acid amplification assays, gene detection with molecular beacons is homogeneous and sensitive, and can be carried out in a sealed tube. Id. A typical Molecular beacon probe is about 25 nucleotides long. In such typical probe, the middle about 15 nucleotides are complementary to the target DNA and do not pair with one another, and the 5 (about 5) nucleotides at each end are complementary to each other and not to the target DNA. However in the present methods, probes that are from 10, 15, or 20 nucleotides long to 30, 40, 50, 60, 70, 80, 100, 150, 200, 300 or up to 500 nucleotides long may be used, and the length of the middle region and the end regions of such probes may be varied. Use of Molecular beacons is particularly advantageous for the detection of SNPs.

In certain embodiments, "double hairpin" probes may be used, and methods of using such probes are described by B. Bagwell, et al. (1994. Nucl. Acids Res. 22, 2424-2425; U.S. Pat. No. 5,607,834), incorporated herein by reference. These structures contain the target binding sequence within the hairpin and therefore involve competitive hybridization between the target and the self-complementary sequences of the hairpin.

In other embodiments, SERS-labeled hybridization probes are used (e.g., SERS no-wash assay). Such probes are discussed in detail in, for example, Natan, Proceedings of the NanoEurope (2008), the disclosure of which is herein incorporated by reference in its entirety. In yet other embodiments, detection methods for use with signal primers described in U.S. Pat. No. 5,550,025 (involving incorporation of lipophilic dyes and restriction sites) and U.S. Pat. No. 5,593,867 (involving fluorescence polarization detection) are used; and the disclosures of U.S. Pat. Nos. 5,550,025 and 5,593,867 are incorporated herein by reference in their entireties.

In certain embodiments, a hybridization probe, such as a molecular beacon, can be used to detect single-stranded nuclei acid products. If a product is double-stranded it may be subjected to heat or other methods of denaturation to convert it to a single-stranded product. In a specific embodiment, a hybridization probe hybridizes to a single-stranded signal extension product, a double-stranded signal extension product subjected to denaturation, but not to a hairpin—containing double-stranded product. A key feature of such products as P1.1 is their lack of hairpin structures that would impede detection of target sequences by means of fluorogenic hybridization probes such as molecular beacons. As a result of this lack of hairpins, a mutation (e.g., a single nucleotide difference or SNP) or a sequence variation in such secondary LAMP product can be detected by molecular beacons or other probe (e.g., SNP sensitive probe). Also, Molecular beacons can bind to P1.3 (see FIG. 2B) or P2.2.2.1.3 (see FIG. 5), if such sequences are subjected to heat denaturation. Molecular Beacons can also bind P1.2 because the D sequence in P1.2 is single-stranded (see FIG. 2B). In other embodiments, Molecular beacons preferentially bind to such extension products as P2.2.2.1.1 (see FIG. 5) because such product is single-stranded.

In some embodiments, the secondary LAMP products may be detected in post-amplification formats. In such embodiments, hybridization probes described herein are added to the reaction mixture upon completion of the LAMP amplification reaction described herein. In some embodiments, hybridization probes are added at least 5, 10, 15, 20, 30, 45 minutes or 1 hour after initiation of the LAMP reaction described herein. In other embodiments, hybridization probes are added to the reaction after termination of the amplification reaction. In some embodiments, the LAMP reaction is stopped by heat denaturation prior to addition of a hybridization probe, e.g., a Molecular beacon.

In yet other embodiments, the secondary LAMP products may be detected during the amplification reaction. In some embodiments, hybridization probes described herein are added to the reaction mixture at the same time as at least one signal primer. In yet other embodiments of the present method, at least one LAMP amplification primer, at least one signal primer and at least one hybridization probe are added simultaneously to the reaction.

In one embodiment, the signal primers used in the present methods may themselves function as reporter groups.

In certain embodiments, the 5' end of the signal primer may comprise a sequence which does not hybridize to the target sequence but which contains special nucleotide sequences (often involving structural features) which facilitate detection or capture of the secondary amplification product. Examples of chemical modifications include affinity ligands (e.g., avidin, streptavidin, biotin, haptens, antigens and antibodies) and reporter groups (labels, e.g., radioisotopes, fluorescent dyes, enzymes which react to produce detectable reaction products, and visible dyes). Examples of special nucleotide sequences include (i) sequences which will form a triple helix by hybridization of a labeled oligonucleotide probe to the double stranded secondary amplification product, and (ii) recognition sites for double-stranded DNA binding proteins which become capable of binding the double-stranded DNA binding protein when rendered double stranded during amplification (e.g., repressors, regulatory proteins, restriction endonucleases, RNA polymerase).

In one embodiment, the signal primer may contain either a capture group or a reporter group, and the target sequence itself or an amplification primer may optionally provide a second capture or reporter group. Alternatively, when both a capture and reporter group are required, the signal primer may contain both a capture and a reporter, group which act in conjunction only when the signal oligonucleotide becomes double-stranded. This structure is formed only when the presence of target sequences induces priming, extension, displacement and re-priming. Such bi-functional signal primers may also form the basis for a variety of homogeneous detection methods such as fluorescence anisotropy or fluorescence energy transfer.

When the methods employ two signal primers which hybridize to opposite strands of a double stranded target sequence, one of the signal primers may comprise a special nucleotide sequence or chemical modification to facilitate capture or immobilization of the secondary amplification product and the other may contain a detectable reporter group or label for detection of the captured or immobilized secondary amplification product. The use of labels and reporter groups for detecting nucleic acids as well as the use of ligands, chemical modifications and nucleic acid structural features for capture or immobilization of nucleic acids is well known in the art.

In one embodiment, the signal primers used in the present methods may themselves function as a reporter group. In some embodiments, sequence S1 of primer FSP and/or sequence S2 of primer RSP (see FIGS. 1, 2B, 3B, 4, 5 and 6) may function as reporter groups. In a certain embodiment, a reporter group of a signal primer contains a fluorophore. In a specific embodiment, a reporter group of a signal primer contains a fluorogenic hairpin. In other embodiments, a reporter group of a signal primer is not a fluorogenic hairpin. In one embodiment, the signal primer contains a reporter group (e.g., a fluorogenic label) wholly or partially at one end of a single-stranded region of the signal primer and a target-binding sequence at another end of a single-stranded region of the signal primer. In yet another embodiment, the target-binding sequence of a signal primer is contained in the middle of two fluorophore-containing regions of a signal primer, such that a target-binding sequence is contained within the intramolecularly base-paired secondary structure prior to its hybridization to the target.

Fluorogenic hairpin technology was described in U.S. Pat. No. 5,928,869, which is incorporated herein by reference in its entirety. Such technology employs a detector oligonucleotide for detection of nucleic acid target sequences by reducing fluorescence quenching in a target-dependent manner. In such method, the target binding sequence is located wholly or partially in a single-stranded "tail" region. The secondary structure (e.g., a hairpin) therefore need not unfold in order to initially hybridize to the target. The detector oligonucleotides form an intramolecularly base-paired secondary structure and contain a donor/acceptor dye pair linked such that fluorescence quenching occurs in the absence of target. Unfolding or linearization of an intramolecularly base-paired secondary structure in the detector oligonucleotide in the presence of the target increases the distance between the dyes and reduces fluorescence quenching. Unfolding of the base-paired secondary structure typically involves intermolecular base-pairing between the sequence of the secondary structure and a complementary strand such that the secondary structure is at least partially disrupted. In one of the embodiments of such technology, a restriction endonuclease recognition site (RERS) is present between the two dyes such that intermolecular base-pairing between the secondary structure and a complementary strand also renders the RERS double-stranded and cleavable or nickable by a restriction endonuclease. Cleavage or nicking by the restriction endonuclease separates the donor and acceptor dyes onto separate nucleic acid fragments, further contributing to decreased quenching.

In one embodiment, the sequence S1 of primer FSP and/or sequence S2 of primer RSP contains a fluorogenic hairpin. If sequence S1 of primer FSP contains a fluorogenic hairpin, it will become unfolded during the extension process as shown in FIG. 2B (extension product P1.3), FIG. 4 (extension product P2.2.2.1), FIG. 5 (extension product P.2.2.2.1.2 and P.2.2.2.1.3) or FIG. 6 (extension product P2.2.2.1.1c), and will thus produce a fluorescent signal.

Contemplated herein are methods of detection of target amplification via a signal primer or primers containing a reporter group, such as S1 or S2, wherein the reporter group may contain a fluorescent label, and wherein such reporter group produces fluorescent signal when double-stranded, but is inert when single-stranded. For example, in such embodiments, a reporter group will produce a fluorescent signal when product P.2.2.2.1.3 (see FIG. 5) or product P.2.2.2.1.1c (see FIG. 6) are generated.

Further, fluorogenic secondary products may also be produced with hairpin-bearing primers that hybridize and are extended from target sites R4 and F4 (see FIGS. 1-5).

In any of the methods employing fluorescence quenching technology, associated change in a fluorescence parameter (e.g., an increase in donor fluorescence intensity, a decrease in acceptor fluorescence intensity or a ratio of fluorescence before and after unfolding) can be monitored as a indication of the presence of the target sequence.

In one embodiment, a hybridization probe or a reporter group may produce a luminescent signal.

Alternatively, in other embodiments, the signal primer may be unmodified, e.g., without reporter groups, capture groups or structural features to facilitate detection or capture of the secondary amplification products. The secondary amplification products may then be detected based on their size, e.g., by gel electrophoresis and ethidium bromide staining.

The present methods can greatly simplify the procedures for primer-based detection methods, which previously relied on two consecutive amplification reactions to attain high sensitivity and specificity, the second reaction being performed with internally nested signal-generating amplification primers.

5.4. Kits for Generation and Detection of Secondary Lamp Products

Provided herein are kits for generation and detection of nucleic acid detection products and secondary LAMP products, comprising (i) a nucleic acid signal primer, wherein at least a portion of the nucleic acid signal primer hybridizes to a first target sequence region, (ii) a nucleic acid amplification primer, wherein the amplification primer comprises a 3' terminal portion which hybridizes to a second target sequence region upstream of the first target sequence region to which the signal primer hybridizes and a 5' terminal portion which comprises substantially the same nucleotide sequence as a third region of the target sequence downstream of the second target sequence region to which the 3' terminal portion hybridizes, and (iii) a displacement primer, which hybridizes to a fourth target sequence region upstream of the second target sequence region to which the 3' terminal portion of the nucleic acid amplification primer hybridizes.

Also provided herein are kits for generation and detection of nucleic acid detection products and secondary LAMP products, comprising a first component and a second component, wherein the first component comprises LAMP reaction ingredients and the second component comprises ingredients for production of nucleic acid detection products and secondary LAMP products. In one such embodiment, the first component of the kit comprises (i) a n amplification primer, wherein the amplification primer comprises a 3' terminal portion which hybridizes to a first region of the target sequence and a 5' terminal portion which comprises substantially the same nucleotide sequence as a second region of the target sequence downstream of the second target sequence region to which the 3' terminal portion hybridizes, and (ii) a displacement primer, which hybridizes to a third target sequence region upstream of the first target sequence region to which the 3' terminal portion of the nucleic acid amplification primer hybridizes.

In such embodiments, the second component of the kit can comprise a nucleic acid signal primer, wherein at least a portion of the nucleic acid signal primer hybridizes to a fourth target sequence region, which is located downstream of the first target sequence region to which the amplification primer hybridizes. In one embodiment, (the first component contents can be combined and the LAMP reaction initiated. In one such embodiment, the reaction is initiated by addition of DNA polymerase possessing strand displacement activity. Further, in such embodiments, the second component can be added, e.g., added later, to the reaction mix, e.g., after 30 seconds of reaction initiation, after about 1 minute of reaction initiation, after 1.5 minutes, after 2 minutes, after 3 minutes, after 4 minutes, after 5 minutes, 6, 7, 8, 9, 10, 11, 12, 3, 14, 15, 20, 25, 30, 35, 40, 45 minutes or up to 1 hour after the LAMP reaction initiation. In yet another embodiment, the first component and the second component are combined prior to the initiation of the LAMP reaction. In yet another embodiment, the first component and the second component are combined at the time of the initiation of the reaction, e.g., wherein the first component, the second component and DNA polymerase are combined to start the amplification reaction.

In certain embodiments, any of the kits can further comprise (i) a second nucleic acid signal primer that hybridizes to a second target sequence, (ii) a second nucleic acid amplification primer that hybridizes to the second target sequence, and (iii) a second displacement primer that hybridizes to the second target sequence.

In another embodiment, any of the kits can further comprise (i) a third nucleic acid signal primer that hybridizes to a third target sequence, (ii) a third nucleic acid amplification primer that hybridizes to the third target sequence, and (iii) a third displacement primer that hybridizes to the third target sequence. In yet another embodiment, any of the kits can further comprise (i) a fourth nucleic acid signal primer that hybridizes to the fourth target sequence, (ii) a fourth nucleic acid amplification primer that hybridizes to the fourth target sequence, and (iii) a fourth displacement primer that hybridizes to the fourth target sequence. Further, contemplated herein are kits wherein 5, 6, 7 or more target sequences are amplified and detected using the present methods.

In one embodiment, any of the kits can further comprise a hybridization probe. In one specific embodiment, the hybridization probe is a molecular beacon.

In some embodiments, the signal primer in any of the above-described kits further comprises a reporter region. In one embodiment, such a reporter group produces a fluorescent signal. In one specific embodiment, the reporter group is a fluorogenic hairpin. In one embodiment, the nucleic acid target sequence in any of the above-described kits is a sequence of *Mycobacterium tuberculosis*.

5.5. Uses of Kits and Methods

The methods and kits described herein can allow, for example, multiplex detection of two or more (potential) targets or sequence variants. Specifically, the present methods and kits can allow such detection of (potential) targets in a real-time and single, closed-tube formats.

Applications of the present methods can include, e.g., detection of genetic material of interest in a sample, for example, detection of particular microbial nucleic acids in a sample. Applications can include, for example, diagnosis of infectious diseases, genetic disorders and genetic traits. Specifically, the methods and kits presented herein may be used in any biological or clinical application wherein the real-time detection of a gene, a gene sequence, a mutation in a gene (e.g., a deletion, an insertion, a point mutation or an SNP) in a biological sample is desired. More specifically, the kits and methods can be particularly advantageous where detection of two or more genes, gene sequences, or mutations in a gene or genes in a biological sample is desired.

For example, in one exemplary, non-limiting example one application of the methods and kits presented herein is detection of bacterial, viral or parasitic nucleic acid in a sample, e.g., a patient sample. For example, the methods and kits presented herein can be used in the detection of mutations associated with drug resistance in bacteria. In one specific embodiment, the methods and kits described herein may be used to detect presence of mycobacteria (e.g., *M. tuberculosis, M. avium, M. leprae, M. africanum, M. intracellulare, M. smegmatis, M. microti, M. bovis, M. fortuitum*, and/or *M. peregrinum*) or detect drug resistant mutations in mycobacteria. Mycobacteria are responsible for considerable human morbidity and mortality worldwide, specifically as a consequence of resurgent infections caused by *M. tuberculosis* and the emergence of *M. avium* complex (MAC) disease in patients with AIDS (see Musser, Clin. Microbiol. Reviews 8(4):496-514 (1995)). In a more specific example, the methods and kits herein described may be used for the detection of drug resistant mutations in *M. tuberculosis* as described in Examples 1 and 2.

Thus, the methods and kits presented herein may be used to diagnose tuberculosis, and/or other infectious diseases associated with mycobacteria, to diagnose presence or absence of drug-resistant strains of mycobacteria and/or identify specific mutations responsible for such drug resistance. In another specific embodiment, the present methods may be used for simple and cost-effective diagnosis of MAC or other infectious disease in a patient, and/or to identify the basis of microbial resistance of MAC in a patient. In one embodiment, the patient is a human. In another embodiment, the patient is an AIDS patient.

The following examples are set forth to assist in understanding the subject matter presented here and should not be construed as specifically limiting the invention described and claimed herein. Such variations of the invention, including the substitution of all equivalents now known or later developed, which would be within the purview of those skilled in the art, and changes in formulations or minor changes in experimental design, fall within the scope herein.

6. EXAMPLES

6.1 Example 1

This example illustrates use of a signal primer and the methods presented herein in a LAMP reaction to generate a nucleic acid detection product that facilitates detection of mutations in the rpoB gene associated with the resistance of *Mycobacterium tuberculosis* to the antibiotic Rifampin.

Figure 7:
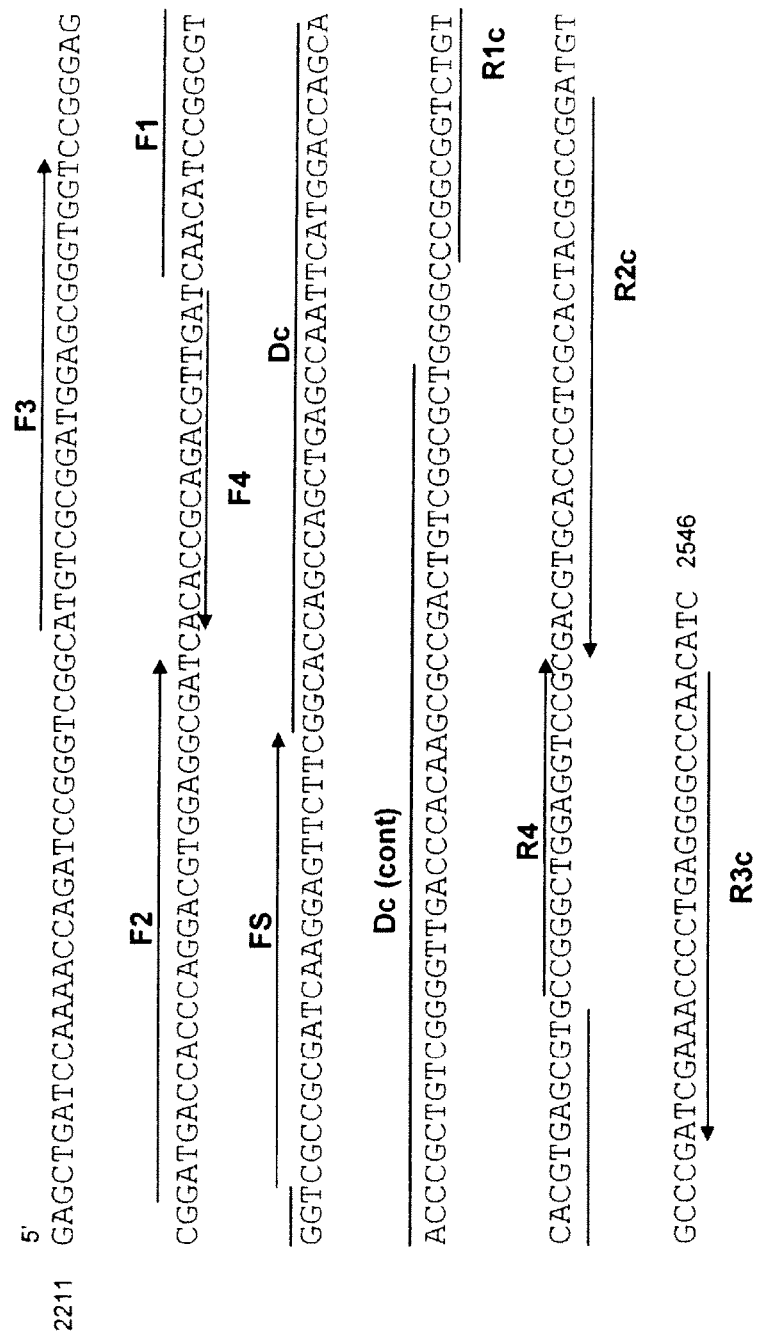
FIG. 7 shows a region of the *M. tuberculosis* rpoB gene (SEQ ID NO: 36).

FIG. 7 shows a region of the *M. tuberculosis* rpoB gene to be amplified by LAMP (only one of the two complementary target strands is shown; GenBank accession no: L27989, nucleotides 2211-2546). Sequences recognized by the various primers are indicated (designations are those used in FIGS. 1-6a), as is the target region of interest (Dc). In this example, Dc represents an 81 nucleotide "core" sequence that encodes the active site of RNA polymerase enzyme in *M. tuberculosis*. Ninety-five percent of *M. tuberculosis* strains known to be resistant to the antibiotic Rifampin contain mutations within this core sequence. Furthermore, all known mutations in this core sequence are known to be associated with rifampin resistance in *M. tuberculosis* (Musser, Clin. Microbiol. Rev. 8, 496-514, 1995, incorporated herein by reference). The majority of these resistance-associated mutations are single-nucleotide changes.

LAMP primers to the rpoB target sequence were designed in view of guidelines provided on the Eiken Genome Site (http://loopamp.eiken.co.jp/e/lamp/index.html). So-called loop primers, which accelerate the overall LAMP reaction as described by Nagamine et al. (Molecular and Cellular Probes (2002) 16, 223-229), were designed to recognize loop sequences F4 and R4. The signal primer was designed to recognize a sequence complementary to region depicted as FS in FIG. 7.

The DNA oligonucleotide sequences for the various primers are as follows:

```
Forward LAMP primer, FLP (Seq ID No 1):
5' ACCACCGGCCGGATGTTGGATGACCACCCAGGACGTGGAGGCGAT Reverse LAMP primer, RLP (Seq ID No 2):
5' CCGGCGGTCTGTCACGTGAaGGCCGTAGTGtGACGGGTGCACGT Forward outer primer, F3 (Seq ID No 3):
5' CGGGTCGGCATGTCGCGGATGGAGC Reverse outer primer, R3 (Seq ID No 4):
5' CCCTCAGGGGTTTCGATCGGGCACAT Forward signal primer, FSP (Seq ID No 5):
5' CGCCGCGATCAAGGAGTTCTTC Forward loop primer, FLoop(F4) (Seq ID No 6):
5' ATCAACGTCTGCGGTGT Reverse loop primer, RLoop (R4) (Seq ID No 7):
5' CCGGGCTGGAGGTCCGC
```

Nucleotides depicted by lower case letters in Seq ID No 2 (Reverse LAMP primer) differ from the GenBank sequence at those nucleotide positions. These changes were designed into the primer in order to disrupt potentially problematic secondary structure within the primer, while still permitting hybridization to and loop-mediated amplification of the target sequence.

Under reaction conditions suitable for LAMP (see below), this collection of primers amplifies the desired target region (D and its complementary sequence, Dc) bearing the 81 by core of rpoB, through the series of extension and displacement steps depicted in FIGS. 1-6. The presence of signal primer, FSP, in these reaction steps, results in formation of molecule P2.2.2.1.1 and its complementary strand (P2.2.2.1.1c) (FIG. 6). These secondary LAMP products each contain a single copy of the 81 nucleotide rpoB core sequence (either strand), which may or may not contain mutations associated with rifampin resistance, depending on whether such mutations were present in the genomic target sequence, prior to amplification. A key feature of these secondary LAMP products is the absence of potential hairpins that would cover the rpoB core sequence and thereby hinder detection of this target sequence by means of conventional hybridization-based probes such as Molecular beacons.

As described by El-Hajj et al. (J. Clin. Micro. 39, 4131-4137 (2001), incorporated herein by reference), a set of 5 differentially labeled molecular beacons may be used to detect the presence of any mutation within the 81 rpoB core sequence, in a closed, single-tube assay. The assay relies on the fact that molecular beacons only hybridize to target sequences that are perfectly complementary to the probe. Thus a fluorescence signal is only produced when a target sequence is perfectly complementary to the probe—as little as a single nucleotide change in the target sequence will prevent the molecular beacon from binding, leaving the beacon folded in a non-fluorescent hairpin state. The presence of any mutation within the 81 bp core sequence may be detected by employing a combination of 5 molecular beacons that together span the entire core sequence, with each beacon bearing a different colored fluorophore and each designed to be complementary to the wild-type sequence within a different segment of the core sequence. In the presence of wild-type target, all molecular beacons will bind to their respective target segments, and—with each beacon fluorescing a different color—five distinct fluorescent signals will result. A mutation in any given segment will preclude binding of the beacon corresponding to that segment and leading to an absence of the corresponding fluorescent signal, while beacons corresponding to the remaining wild-type segment will continue to bind target and fluoresce. Thus absence of any one of the 5 fluorescent signals indicates the presence of rifampin resistant M. tuberculosis. The presence of signals from all 5 molecular beacons indicates sensitivity to rifampin.

The following molecular beacons (taken from J. Clin. Micro. 39, 4131-4137 (2001)) may be used to detect mutations in the rpoB sequence contained in LAMP secondary products.

```
Probe A (SEQ ID NO: 31):
5'-Texas red-TTTTTT-fluoresescein-

CGAGCTCAGCTGGCTGGTGCCTCG-dabcyl-3'

Probe B (SEQ ID NO: 32):
5'-tetrachlorofluorescein-

GCTACGAGCCAATTCATGGACCAGACGTAGC-dabcyl 3'

Probe C (SEQ ID NO: 33):
5'-tetramethylrhodamine-TTTTTT-fluorescein-

CCGACGCCGACAGCGGGTTGTTCGTCGG-dabcyl-3'

Probe D (SEQ ID NO: 34):
5'-rhodamine-TTTTTT-fluorescein-

CCACGCTTGTGGGTCAACCCCGTGG-dabcyl-3'

Probe E (SEQ ID NO: 35):
5'-fluorescein-

CCTGCCGCCGACTGTCGGCGCTGGCAGG-dabcyl-3'
```

The underlined sequence of each probe is complementary to wild-type sequence within the rpoB core. Probes A, C and D hybridize to strand Dc of the wild-type sequence, while Probes B and E bind to strand D or the wild-type sequence. Molecular beacons other than those listed above may be used in place of those shown here. It may be possible to cover the 81 bp core sequence with fewer than 5 molecular beacons. The key feature is that, taken together, the combination of molecular beacons should span the 81 bp core sequence and that each individual beacon (or probe) must be capable of distinguishing any single-nucleotide changes within the sequence of its intended target segment. For a single-tube assay, each beacon must also be labeled with a dye that can be distinguished from the dyes labeling the other beacons used in the assay.

A closed-tube, homogenous assay for mutations within the 81 bp core sequence of the rpoB gene may be performed as follows: Genomic DNA from M. tuberculosis is prepared from bacteria contained in sputum samples or positive growth cultures as described by Down et al. (J. Clin. Micro. 34, 860-865. (1996)). Resulting genomic DNA samples are then subjected to LAMP amplification reactions. Amplification may be performed in 96 well microtiter plates with each well containing a total reaction volume 50 uL consisting of the following components: 1 M betaine (Sigma), 20 mM Tris-HCl (pH 8.8), 10 mM KCl, 10 mM $(NH_4)_2$ $SO_4$, 4 mM $MgSO_4$; 0.1% tritonX-100; 400 uM each of dATP, dCTP, dGTP, and dTTP; 16 units of Bst DNA polymerase target fragment (New England Biolabs); primers FLP and RLP, 800 nM each; primers F3 and F4, 200 nM each; loop primers F4 and R4, 400 nM each; signal primer FSP, 800 nM; molecular beacon Probes A, B, C, D, and E, 200 nM each; and Target sample (SuL). Following assembly of all components, reaction wells are hermetically sealed prior to incubation at 60 deg. C. on an Applied Biosystems 7700 Prism spectrofluorimetric thermocycler. Amplification is carried out for 60 min, and fluorescence is measured in each well throughout the course of the amplification reaction. The background fluorescence of each probe is determined from readings taken between the $3^{rd}$ and $6^{th}$ minute following commencement of amplification, and these values are used as a baseline for each probe.

After the mixtures have incubated for 60 min at 60 deg C., it may be advantageous to heat the reaction mixtures to 90 deg C. briefly, which terminates the LAMP process, and may facilitate hybridization of the molecular beacon probes to the LAMP secondary products resulting from the signal primer.

Results expected from the LAMP assay of a variety of known rpoB mutations are shown in Table 1.

TABLE 1

LAMP assay results expected for various known mutations of rpoB*

| rpoB* genotype (codon change) | Fluorescent signal indicating hybridization of Molecular beacon | | | | | Susceptibility to Rifampin determined by Assay |
|---|---|---|---|---|---|---|
| | Probe A | Probe B | Probe C | Probe D | Probe E | |
| 1294-1299 deletion GGCACC (433-434) | no | yes | yes | yes | yes | resistant |
| 1305G > T (Gln435His) | no | yes | yes | yes | yes | resistant |
| 1307T > C (Leu436Pro) | no | yes | yes | yes | yes | resistant |

TABLE 1-continued

LAMP assay results expected for various known mutations of rpoB*

| rpoB* genotype (codon change) | Fluorescent signal indicating hybridization of Molecular beacon | | | | | Suscep- tibility to Rifampin deter- mined by Assay |
|---|---|---|---|---|---|---|
| | Probe A | Probe B | Probe C | Probe D | Probe E | |
| 1310G > C (Ser437Thr) | yes | no | yes | yes | yes | resistant |
| 1313A > T (Gln438Leu) | yes | no | yes | yes | yes | resistant |
| 1320G > A (Met440Ile) | yes | no | yes | yes | yes | resistant |
| 1322A > T (Asp441Val) | yes | no | yes | yes | yes | resistant |
| 1340C > T (Ser447Leu) | yes | yes | no | yes | yes | resistant |
| 1351C > T (His451Tyr) | yes | yes | yes | no | yes | resistant |
| 1351C > G (His451Asp) | yes | yes | yes | no | yes | resistant |
| 1367C > T (Ser456Leu) | yes | yes | yes | yes | no | resistant |
| 1373T > C (Leu458Pro) | yes | yes | yes | yes | no | resistant |
| Wild type | yes | yes | yes | yes | yes | sensitive |

*Note: mutations listed in Table 1 are taken from Musser, Clin Microbiol. Rev., 1995, 496-514; however, the numbering scheme provided in that publication is designated on the basis of alignment of the translated E. coli rpoB sequence with a portion of the M. tuberculosis sequence (provided original by Telenti et al. (Lancet 341, 647-650, 1993), and are not the true positions of the actual M. tuberculosis codons/nucleotides. The numbering system in Table 1 has been corrected to reflect the actual positions of nucleotides and codons within rpoB of M. tuberculosis, using the complete gene sequence of rpoB as the reference sequence (determined by Miller et al., Antimicrob. Agents Chemother. 38, 805-811, (1994); GenBank accession no. L27989). Positions of the mutations as shown in Table 1 are relative to the 1st nucleotide of the 1st codon in the M. tuberculosis sequence. Table 2 contains a comparison the number schemes of Telanti/Musser and Miller et al. Also shown in Table 2 is the molecular beacon probe designed to detect (by failing to hybridize) mutations in the indicated codons.

TABLE 2

Comparison of rpoB numbering systems

| Codon numbering of Musser/ Telenti et al | Codon numbering of Miller et al (GenBank acc. no. L27989) | Nucleotide positions in GenBank Ref Seq. (accession # L27989), which includes 1064 non-coding nucleotides prior to the first codon. | Coding Nucleotides (numbered beginning with first nucleotide in first codon) | Molecular Beacon Probe that covers codon |
|---|---|---|---|---|
| 507 | 432 | 2358-2360 | 1294-1296 | Probe A |
| 508 | 433 | 2361-2363 | 1297-1299 | Probe A |
| 510 | 435 | 2367-2369 | 1303-1305 | Probe A |
| 511 | 436 | 2370-2372 | 1306-1308 | Probe A |
| 512 | 437 | 2373-2375 | 1309-1311 | Probe B |
| 513 | 438 | 2376-2378 | 1312-1314 | Probe B |
| 515 | 440 | 2382-2384 | 1318-1320 | Probe B |
| 516 | 441 | 2385-2387 | 1321-1323 | Probe B |
| 521 | 446 | 2400-2402 | 1336-1338 | Probe C |
| 522 | 447 | 2403-2405 | 1339-1341 | Probe C |
| 526 | 451 | 2415-2417 | 1351-1353 | Probe D |
| 531 | 456 | 2430-2432 | 1366-1368 | Probe E |
| 533 | 458 | 2436-2438 | 1372-1374 | Probe E |

6.2. Example 2

This example illustrates use of signal primers in LAMP reactions to facilitate simultaneous detection of mutations associated with isoniazid-resistance in *Mycobacterium tuberculosis*. Mutations in either codon 315 of the katG gene or ribosomal binding site of inhA transcripts are known to account for up to 75% of resistant strains (Piatek et al., 2000, Antimicrob. Agents Chemother. 44: 103-110). By employing two target-specific LAMP reactions and associated signal primers and molecular beacons, the assay described in this example is designed to detect the katG and inhA mutations simultaneously in a single reaction tube. The reaction tube also contains primers and probes for a third LAMP reaction designed to amplify a region of the *M. tuberculosis* gyrB gene as a means of verifying the presence of DNA from the bacterium. LAMP-based detection of the gyrB target is accomplished by displacement (during the LAMP process) of quencher-tagged oligonucleotide hybridized to the 5' end of a fluorescently labeled forward lamp primer.

Figure 8:
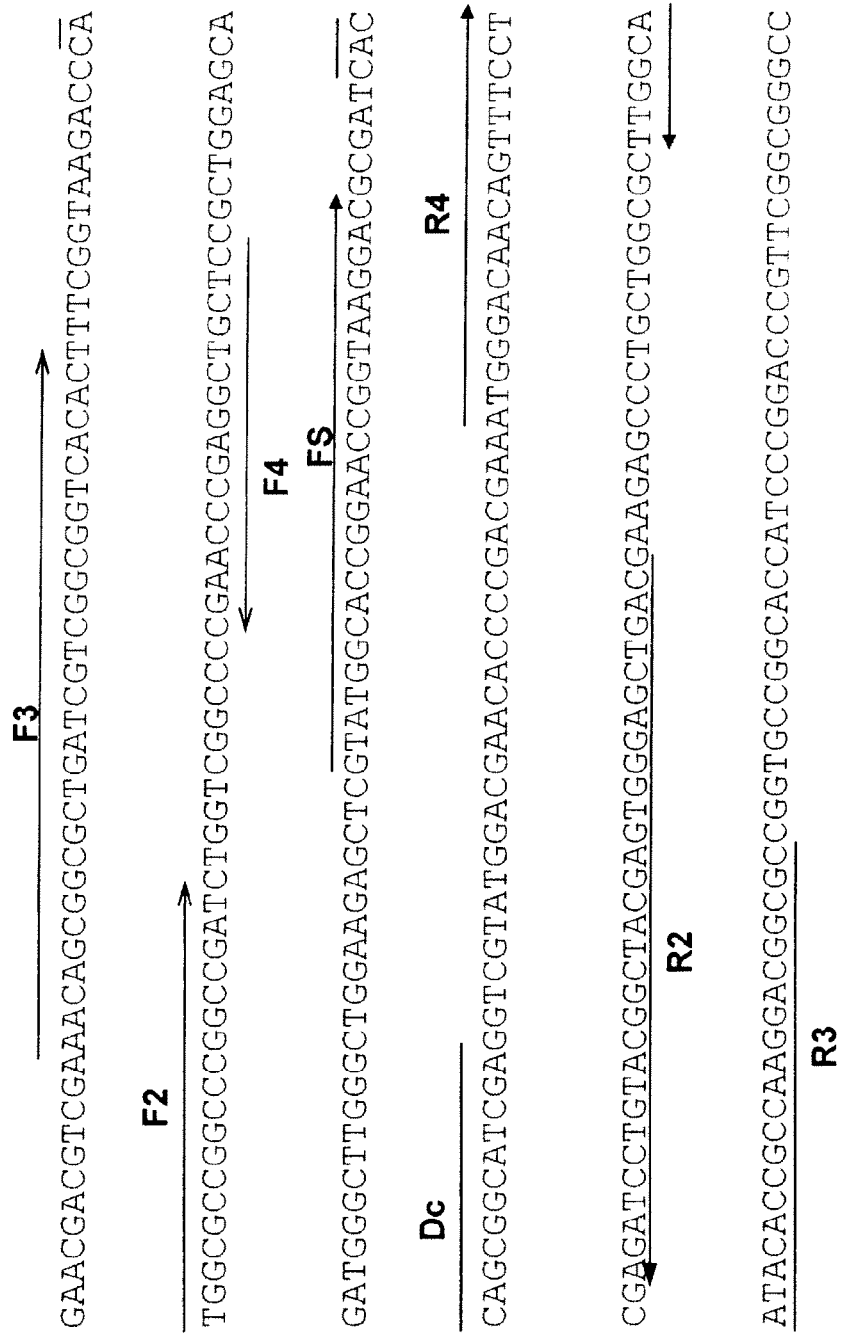
Figure 9:
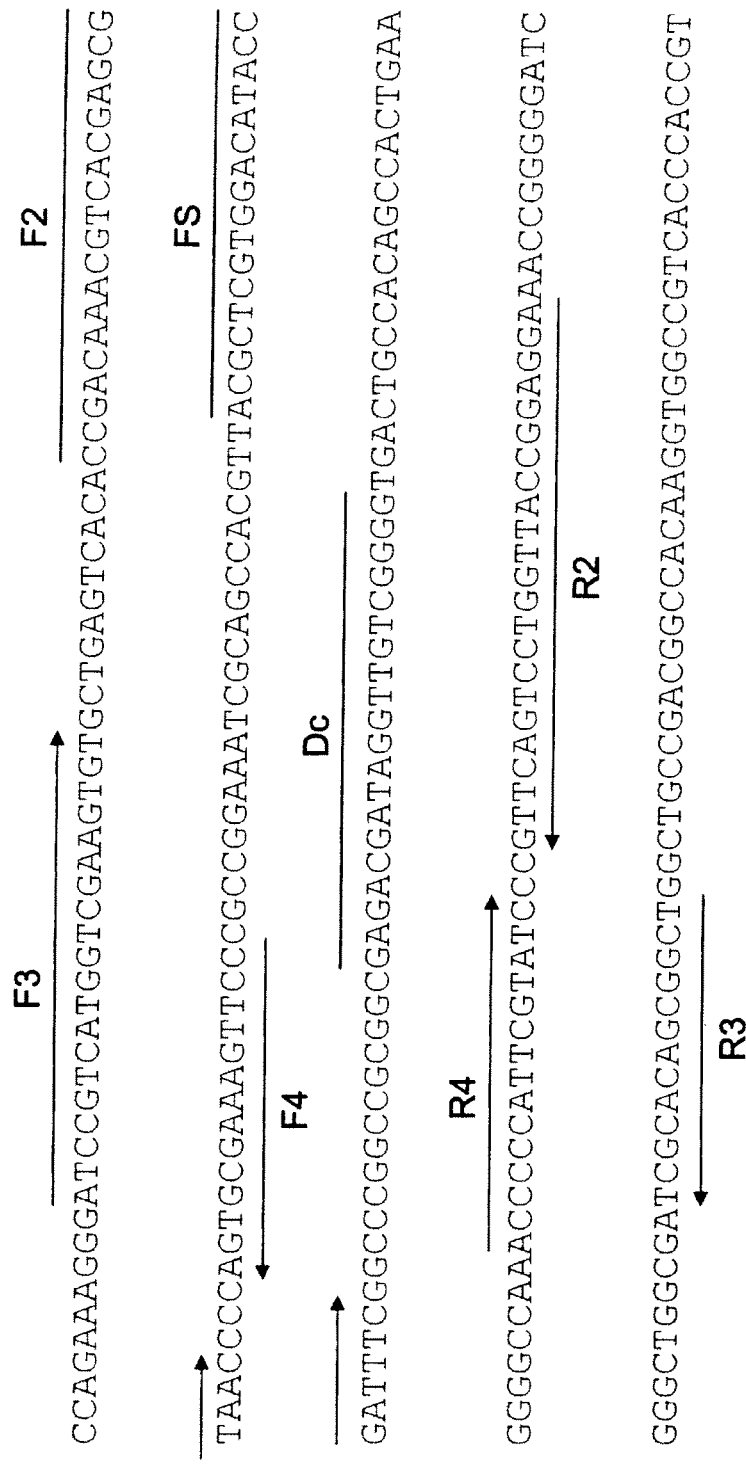
Figure 10:
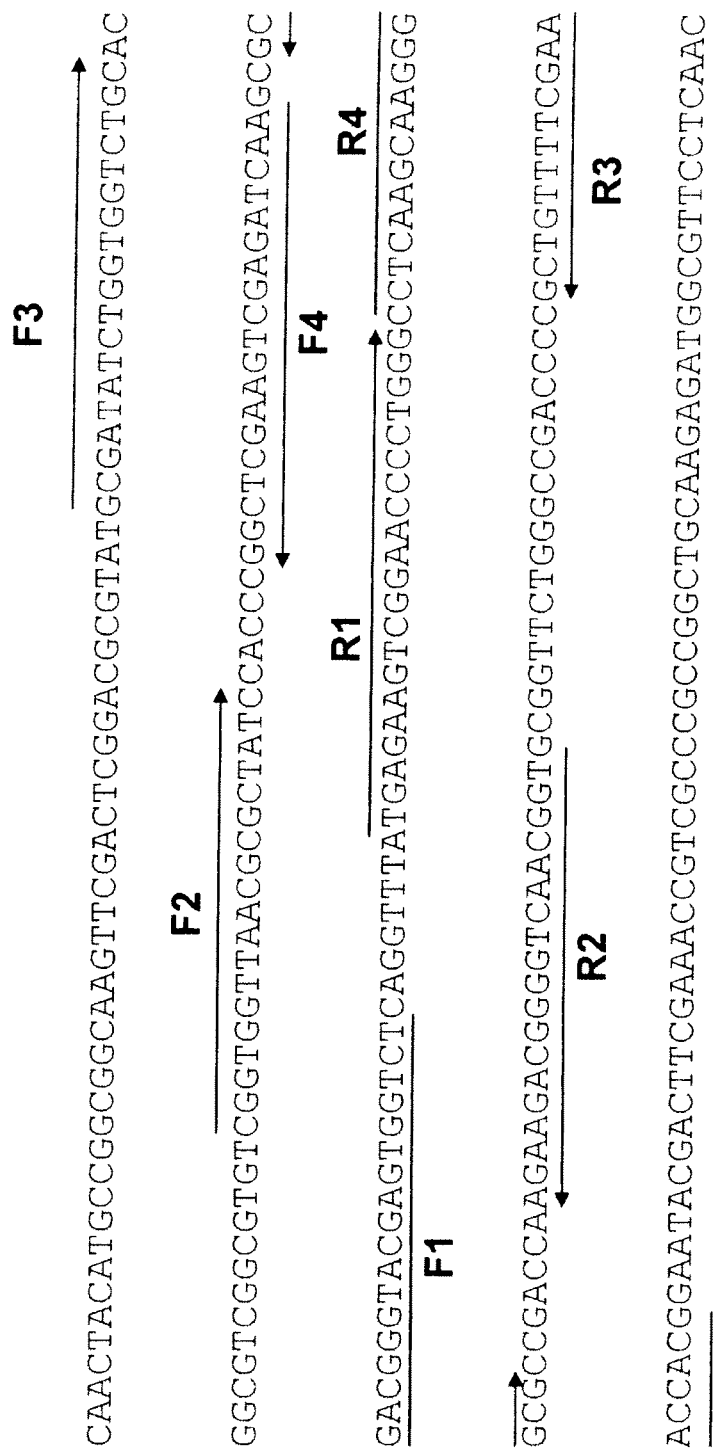

FIGS. 8-10 show regions of the *M. tuberculosis* katG, inhA, and gyrB genes that are to be amplified by LAMP (only one of the two complementary target strands is shown). Sequences recognized by the various primers are indicated (designations are those used in FIGS. 1-6a), as is the target region of interest (Dc). In this example, Dc represents a region of either the katG gene or RBS of inhA known to contain mutations for isoniazid. These resistance-associated mutations are single-nucleotide changes.

LAMP primers to the various target sequence were designed in view of guidelines provided on the Eiken Genome Site (http://loopamp.eiken.co.jp/e/lamp/index.html). So-called loop primers, which accelerate the overall LAMP reaction as described by Nagamine et al. (Molecular and Cellular Probes (2002) 16, 223-229), were designed to recognize loop sequences F4 and R4. The signal primer was designed to recognize a sequence complementary to region depicted as FS in FIGS. 8 and 9.

Table 3 contains a list of the primers and probes used in this Example. Molecular beacons MBP-kat and MBP-inh were taken from Piatek et al. (*Antimicrob. Agents Chemother.* 44, p. 103-110, (2000)). The underlined portion of each molecular beacon is complementary to the wild-type sequence within that target segment. Target sequences containing a mutation in the target segment will not hybridize to the molecular beacon, and will not produce a fluorescent signal. The fluorophores labeling the molecular beacons (MBP-katG and MBP-inh) and primer FLP-gyr are selected so that they may be observed independently within the same tube. One suitable combination of fluorophores in Table 3 is: dye1=fluorescein; dye2=tetrachlorofluorescein; dye3=rhodamine.

With the exception of the flourescent label on FLP-gyrB and the quenching probe, QP-gyr, LAMP primers for the gyrB target were taken from Iwamoto et al. (*J. Clin. Micro.* 41, p. 2616-2622, 2003).

TABLE 3

Oligonucleotides for LAMP-based amplification and detection of katG, inhA, and gyrB targets

| Name | Seq ID No: | Sequence (5'→ 3') | Description |
|---|---|---|---|
| FLP-kat | 8 | CAGCCCAAGCCCATCTGCTCCACATGGCGCCGGCCCGGCCGATCTGGTC | Forward LAMP primer for katG |
| RLP-kat | 9 | TATGGACGAACACCCCGACGAAAGCTCCCACTCGTAGCCGTACAGGATCT | Reverse LAMP primer for katG |
| F3-kat | 10 | ACAGCGGCGCTGATCGTCGGCGGTCACACTT | Forward Outer primer for katG |
| R3-kat | 11 | GCGCCGTCCTTGGCGGTGTATTGCCA | Reverse Outer primer for katG |
| F4-kat | 12 | GAGCAGCCTCGGGTTC | Forward Loop primer for katG |
| R4-kat | 13 | ATGGGACAACAGTTTCCT | Reverse Loop primer for katG |
| FSP-kat | 14 | GTATGGCACCGGAACCGGTAAGGAC | Forward signal primer for katG |
| MBP-kat | 15 | 5'-dye1-CCGAGGCACCAGCGGCATCGACCTGGG-dabcyl-3' | Molecular beacon for katG |
| FLP-inh | 16 | ACGTGGCTGCGATTTCCGGACCGACAAACGTCACGAGCGTAAC | Forward LAMP primer for inhA |
| RLP-inh | 17 | CACAGCCACTGAAGGGGCCATCCTCCGGTAACCAGGACTGAAC | Reverse LAMP primer for inhA |
| F3-inh | 18 | ATCCGTCATGGTCGAAGTGT | Forward Outer primer for inhA |
| R3-inh | 19 | GAGCCAGCCGCTGTGCGATC | Reverse Outer primer for inhA |
| F4-inh | 20 | GGGAACTTTCGCACT | Forward Loop primer for inhA |
| R4-inh | 21 | ACCCCCATTCGTATC | Reverse Loop primer for inhA |
| FSP-inh | 22 | ACGCTCGTGGACATACCGATTTC | Forward Signal primer for inhA |
| MBP-inh | 23 | 5'-dye2-CGAGGCCGACAACCTATCGTCTCCCTCG-dabcyl-3' | Molecular beacon inhA |
| FLP-gyr | 24 | 5'-dye3-AGACCACTCGTACCCGTCGCCGGTGGTTAACGCGCTATC | Forward LAMP primer for gyrB (note 5' dye label) |
| QP-gyr | 25 | 5' GCGACGGGTACGAGTGGTCT-dabcyl-3' | Quencher probe for gyrB (note: binds to 5' end of FLP-gyr) |
| RLP-gyr | 26 | ATGAGAAGTCGGAACCCCTGGGACCGTTGACCCCGTCTTC | Reverse LAMP primer for gyrB |
| F3-gyr | 27 | GCGATATCTGGTGGTCTGC | Forward Outer primer for gyrB |
| R3-gyr | 28 | CGTGGTTTCGAAAACAGC | Reverse Outer primer for gyrB |

TABLE 3 -continued

Oligonucleotides for LAMP-based amplification and detection of katG, inhA, and gyrB targets

| Name | Seq ID No: | Sequence (5'→ 3') | Description |
|---|---|---|---|
| F4-gyr | 29 | TTGATCTCGACTTCGAGCC | Forward Loop primer for gyrB |
| R3-gyr | 30 | CCTCAAGCAAGGGGCG | Forward Loop primer for gyrB |

Under reaction conditions suitable for LAMP (see below), through the series of extension and displacement steps depicted in FIGS. 1-6, this collection of primers will amplify target regions (D and complement, Dc) bearing potential resistance-conferring mutations in codon 315 of katG and the ribosomal binding sequence inhA. The presence of signal primer, FSP, in these reaction steps, results in formation of molecule P2.2.2.1.1 and its complementary strand (P2.2.2.1.1c) (FIG. 6). These secondary LAMP products each contain a single copy of the targeted katG or inhA sequences (either strand), which may or may not contain mutations associated with isoniazid resistance, depending on whether such mutations were present in the genomic target sequence, prior to amplification. A key feature of these secondary LAMP products is the absence of potential hairpins that would cover the targeted sequences and thereby hinder detection by means of conventional hybridization-based probes such as Molecular beacons.

Figure 11:
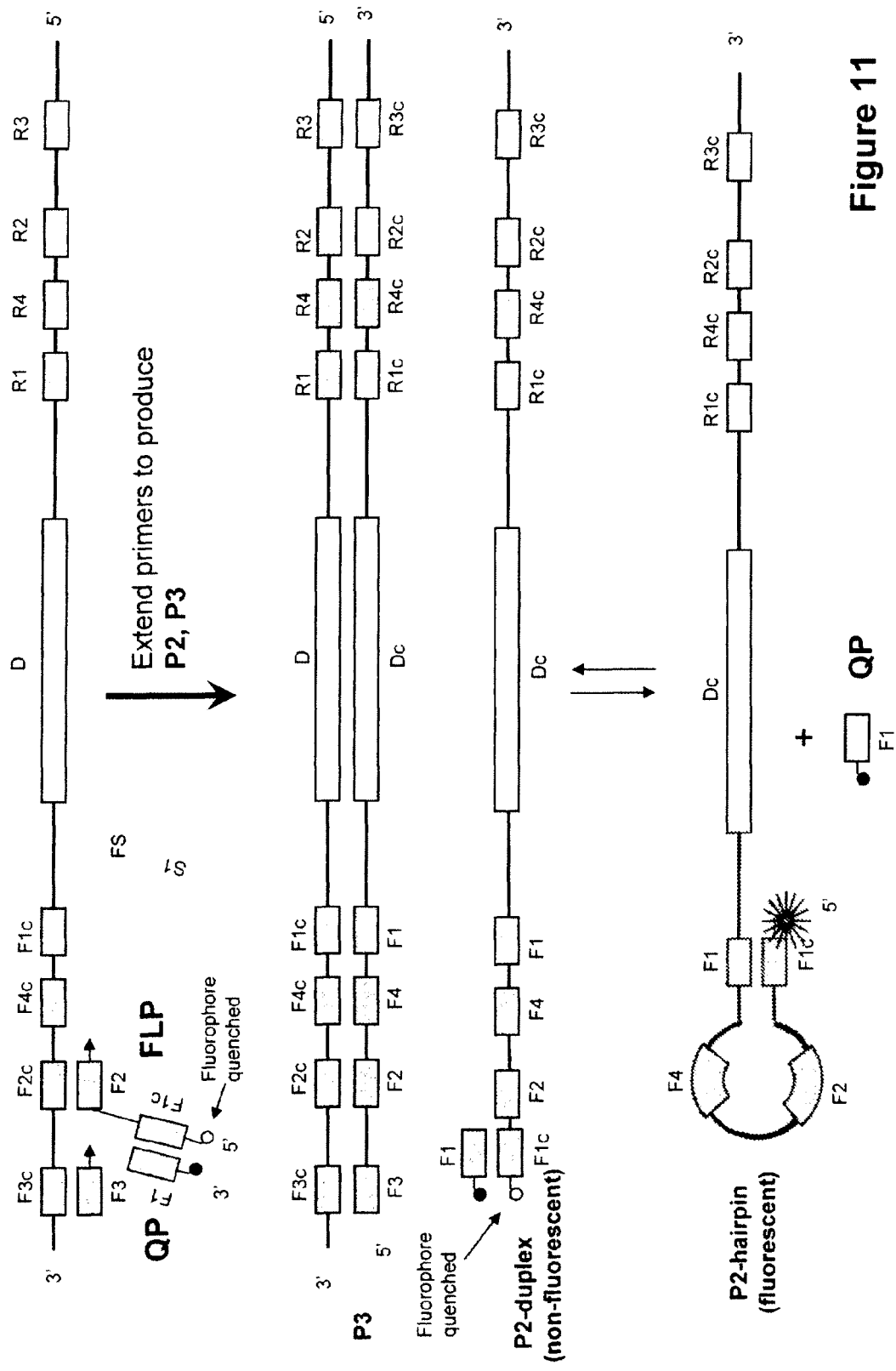

The gyrB target is detected during amplification by a LAMP-mediated separation of a fluorophore/quencher pair linked to FLP-gyr and QP-gyr, respectively. FIG. 11 depicts the steps involved in this process. QP is complementary to the F1c sequence located on the 5' end of FLP, and in the absence of target these two oligonucleotides hybridize to each other, bringing the quencher, dabcyl, into close proximity with fluorophore (dye). In this configuration, fluorescence is quenched. If target is present, FLP is extended and the extension product P2(duplex) is displaced from the template. At this stage, probe QP is still temporarily hybridized to the F1c segment of the FLP extension product. However, an equilibrium will exist between this quenched, duplex form of P2 (P2-duplex), and the hairpin form of the FLP extension product (P2-hairpin). Formation of a hairpin by the FLP extension product results in displacement of quencher probe QP, separating dabcyl from fluorophore and producing a fluorescent signal. In the case of the gyrB LAMP products, a thermodynamic analysis (not shown) indicates that, at equilibrium, the F2-hairpin is strongly favored over F2-duplex provided concentrations of QP are <100 micromolar.

A closed-tube, homogenous assay for mutations within the 81 by core sequence of the rpoB gene may be performed as follows: Genomic DNA from *M. tuberculosis* is prepared from bacteria contained in sputum samples or positive growth cultures as described by Down et al. (*J. Clin. Micro.* 34, 860-865. (1996)). Resulting genomic DNA samples are then subjected to LAMP amplification reactions. Amplification may be performed in 96 well microtiter plates with each well containing a total reaction volume 50 uL consisting of the following components: 1 M betaine (Sigma), 20 mM Tris-HCl (pH 8.8), 10 mM KCl, 10 mM $(NH_4)_2 SO_4$, 4 mM $MgSO_4$; 0.1% tritonX-100; 400 uM each of dATP, dCTP, dGTP, and dTTP; 16 units of Bst DNA polymerase target fragment (New England Biolabs); primers FLP and RLP, 800 nM each; primers F3 and F4, 200 nM each; loop primers F4 and R4, 400 nM each; signal primer FSP, 800 nM; molecular beacons MBP-kat and MBP-inh, 200 nM each; quencher probe QP-gyr, 1600 nM; and Target sample (5 uL). Following assembly of all components, reaction wells are hermetically sealed prior to incubation at 63 deg. C. on an Applied Biosystems 7700 Prism spectrofluorimetric thermocycler. Amplification is carried out for 60 min, and fluorescence is measured in each well throughout the course of the amplification reaction. The background fluorescence of each probe is determined from readings taken between the $3^{rd}$ and $6^{th}$ minute following commencement of amplification, and these values are used as a baseline for each probe.

After the mixtures have incubated for 60 min at 63 deg. C., it may be advantageous to heat the reaction mixtures to 90 deg. C. briefly, which terminates the LAMP process, and may facilitate hybridization of the molecular beacon probes to the LAMP secondary products resulting from the signal primer.

Results expected from the LAMP assay of a variety of known isoniazid resistance-conferring mutations are shown in Table 4.

TABLE 4

LAMP assay results expected for various known mutations in katG and inhA loci

| Genotype of katG codon 315 | Genotype of ribosomal binding sequence in inhA locus | Fluorescent signal of indicated probe/primer | | | Presence of M. tuberculosis DNA detected (gyrB) | Susceptibility to Isoniazid indicated by Assay |
| | | MBP-kat (Dye1) | MBP-inh (Dye2) | FLP-gyr (Dye3) | | |
|---|---|---|---|---|---|---|
| AGC > ACC | Wild type | no | yes | yes | yes | resistant |
| AGC > AAC | Wild-type | no | yes | yes | yes | resistant |
| Wild-type | −16A > T | yes | no | yes | yes | resistant |
| Wild-type | −15C > T | yes | no | yes | yes | resistant |

TABLE 4-continued

LAMP assay results expected for various known mutations in katG and inhA loci

| Genotype of katG codon 315 | Genotype of ribosomal binding sequence in inhA locus | Fluorescent signal of indicated probe/primer MBP-kat (Dye1) | MBP-inh (Dye2) | FLP-gyr (Dye3) | Presence of *M. tuberculosis* DNA detected (gyrB) | Susceptibility to Isoniazid indicated by Assay |
|---|---|---|---|---|---|---|
| Wild-type | −8T > A | yes | no | yes | yes | resistant |
| Wild-type | −8T > G | yes | no | yes | yes | resistant |
| Wild-type | Wild-type | yes | yes | yes | yes | sensitive |
| Wild-type or mutant | Wild-type or mutant | no | no | no | no | Indeterminate result (failed amplification) |

What is claimed is:

1. A method for generating a nucleic acid signal extension product during a loop-mediated isothermal amplification reaction, comprising:
  hybridizing portions of a first nucleic acid signal primer, a first nucleic acid amplification primer, and a first nucleic acid displacement primer to complementary portions of a nucleic acid target sequence,
  wherein the first nucleic acid signal primer hybridizes to the target sequence downstream of the first nucleic acid amplification primer;
  wherein the first nucleic acid amplification primer comprises i) a 3' terminal portion complementary to a portion of the nucleic acid target sequence, and ii) a 5' terminal portion that does not hybridize but is complementary to a portion of the target sequence; and
  wherein the first nucleic acid displacement primer hybridizes to the target sequence upstream of the first nucleic acid amplification primer;
  extending the hybridized first nucleic acid signal primer on the nucleic acid target sequence to produce a first signal extension product;
  extending the hybridized first nucleic acid amplification primer on the nucleic acid target sequence wherein such extension displaces the first signal extension product from the nucleic acid target sequence and produces a first amplification extension product; extending the hybridized first nucleic acid displacement primer, wherein such extension displaces the first amplification extension product from the nucleic acid target sequence and produces a first displacement extension product; and
  detecting the first signal extension product.

2. The method of claim 1, wherein the first signal extension product does not form a self-complementary hairpin structure and is generated concurrently with the first amplification extension product in a loop-mediated isothermal amplification reaction.

3. A method for generating nucleic acid signal extension products during a loop-mediated isothermal amplification reaction, comprising:
  a. hybridizing a first nucleic acid signal primer to a nucleic acid target sequence region, wherein the target sequence comprises at least one self-complementary hairpin structure generated during a loop-mediated isothermal amplification reaction;
  b. extending the hybridized first nucleic acid signal primer on the nucleic acid target sequence to produce a first signal extension product, wherein said first signal extension product comprises a hairpin structure;

c. hybridizing portions of a second nucleic acid amplification primer, as second nucleic acid amplification primer and second nucleic acid displacement primer to complementary portions of the first signal extension product, and extending the second hybridized nucleic acid signal primer on the first signal extension product to produce a second signal extension product;

d. extending the hybridized second nucleic acid amplification primer on the first signal extension product wherein such extension displaces the second signal extension product from the first signal extension product and produces a second amplification extension product;

e. extending the second nucleic acid displacement primer, wherein such extension displaces a second amplification extension product from the first signal extension product and producing a second displacement extension product; and f. detecting the second signal extension product.

4. A method for concurrently generating nucleic acid signal extension products during a loop-mediated isothermal amplification reaction, comprising:

a. hybridizing portion of a first signal primer to a first single stranded target sequence;

b. hybridizing a portion of a first nucleic acid amplification primer to the first single stranded target sequence upstream of the hybridized portion of the first signal primer, wherein the first amplification primer comprises i) a 3' terminal portion complementary to a portion of the first single stranded target nucleic acid sequence, and ii) a 5' terminal portion that does not hybridize but is complementary to a portion of the first single stranded target sequence;

c. hybridizing a first displacement primer to the first single stranded target sequence upstream of the first amplification primer;

d. extending the hybridized first signal primer on the first single stranded target sequence to produce a first signal extension product;

e. extending the hybridized first amplification primer such that it displaces the first signal extension product from the target sequence;

f. extending the hybridized first displacement primer such that it displaces the first amplification extension product from the target sequence;

g. hybridizing a portion of a second signal primer to the displaced first signal extension product;

h. hybridizing a portion of a second amplification primer to the first signal extension product upstream of the hybridized second signal primer, wherein the second amplification primer comprises: i) a 3' terminal portion complementary to a portion of the first signal extension product, and ii) a 5' terminal portion that does not hybridize but is complementary to a portion of the first signal extension product;

i. hybridizing a second displacement primer to the first signal extension product upstream of the second amplification primer;

j. extending the hybridized second signal primer on the first signal extension product to produce a second signal extension product;

k. extending the hybridized second amplification primer on the first signal extension product such that it displaces the second signal extension product from the first signal extension product;

l. extending the hybridized second displacement primer such that it displaces the second amplification extension product from the first signal extension product; and m. detecting the first and second signal extension products.

5. The method of claim 4, wherein two or more target sequences or sequence variants are used concurrently, and wherein two or more nucleic acid signal primers which hybridize to said two or more target sequences are used.

6. The method of claim 5, wherein the two or more target sequences are present in the same contiguous nucleotide sequence or on two different nucleotide sequences.

7. The method of claim 5, wherein the two or more target sequences or sequence variants are derived from at least one organism.

8. The method of claim 4, wherein a second nucleic acid signal primer is hybridized to the second signal extension product, wherein the hybridized second nucleic acid signal primer is extended on the second signal extension product to produce a third signal extension product, wherein the third signal extension product has a hairpin structure on its 5' end; wherein a third nucleic acid signal primer is hybridized to the third signal extension product, wherein the hybridized third nucleic acid signal primer is extended on the third signal extension product to produce a fourth signal extension product, wherein the fourth signal extension product comprises double-stranded nucleic acid, and wherein the fourth signal extension product is detected in real-time.

9. The method of claim 4, wherein a second nucleic acid signal primer is hybridized to the second signal extension product, wherein the hybridized second nucleic acid signal primer is extended on the second signal extension product to produce a third signal extension product, wherein the third signal extension product has a hairpin structure on its 5' end; wherein a third nucleic acid signal primer is hybridized to the third signal extension product, wherein the hybridized third nucleic acid signal primer is extended on the third signal extension product to produce a fourth signal extension product, wherein the fourth signal extension product comprises double-stranded nucleic acid, and wherein the fourth signal extension product is detected in a closed tube format.

10. The method of claim 4, wherein a second nucleic acid signal primer is hybridized to the second signal extension product, wherein the hybridized second nucleic acid signal primer is extended on the second signal extension product to produce a third signal extension product, wherein the third signal extension product has a hairpin structure on its 5' end; wherein a third nucleic acid signal primer is hybridized to the third signal extension product, wherein the hybridized third nucleic acid signal primer is extended on the third signal extension product to produce a fourth signal extension product, wherein the fourth signal extension product comprises double-stranded nucleic acid, and wherein the fourth signal extension product is detected by a hybridization probe selected from the group consisting of a fluorogenic probe, surface enhanced Raman scattering (SERS)-labeled probe, a single nucleotide difference sensitive probe, and a molecular beacon probe.

11. The method of claim 4, wherein a second nucleic acid signal primer is hybridized to the second signal extension product, wherein the hybridized second nucleic acid signal primer is extended on the second signal extension product to produce a third signal extension product, wherein the third signal extension product has a hairpin structure on its 5' end; wherein a third nucleic acid signal primer is hybridized to the third signal extension product, wherein the hybridized third nucleic acid signal primer is extended on the third signal extension product to produce a fourth signal extension product, wherein the fourth signal extension product comprises double-stranded nucleic acid, wherein the signal primer comprises a hybridization region and a reporter region, wherein the hybridization region hybridizes to the region of the nucleic acid target sequence, and wherein the first, second, third, or fourth signal extension product is detected based on the reporter region.

12. The method of claim 4, wherein a second nucleic acid signal primer is hybridized to the second signal extension product, wherein the hybridized second nucleic acid signal primer is extended on the second signal extension product to produce a third signal extension product, wherein the third signal extension product has a hairpin structure on its 5' end; where in a third nucleic acid signal primer is hybridized to the third signal extension product, wherein the hybridized third nucleic acid signal primer is extended on the third signal extension product to produce a fourth signal extension product, wherein the fourth signal extension product comprises double-stranded nucleic acid, and wherein the fourth signal extension product is detected based on a modification to facilitate capture of the signal product incorporated into one of the signal primers.

13. The method of claim 1 wherein said method is used for detecting drug resistant tuberculosis.

14. The method of claim 4, wherein a second nucleic acid signal primer is hybridized to the second signal extension product, wherein the hybridized second nucleic acid signal primer is extended on the second signal extension product to produce a third signal extension product, wherein the third signal extension product has a hairpin structure on its 5' end; where in a third nucleic acid signal primer is hybridized to the third signal extension product, wherein the hybridized third nucleic acid signal primer is extended on the third signal extension product to produce a fourth signal extension product, wherein the fourth signal extension product comprises double-stranded nucleic acid, and wherein the first, second, third, or fourth extension product is detected post-amplification.

15. The method of claim 1, wherein the signal primer comprises a hybridization region and a reporter region.

16. The method of claim 2, wherein the reporter region is a fluorogenic hairpin.

17. The method of claim 1, wherein the first signal extension product is detected in real time.

18. The method of claim 1, wherein the first extension product is detected in a closed-tube format.

19. The method of claim 1, wherein the first signal extension product is detected by providing a modification in the nucleic acid signal primer to facilitate capture of the first signal extension product.

20. The method of claim 1, wherein the first signal extension product is detected by a hybridization probe selected from the group consisting of fluorogenic probe, single nucleotide difference sensitive probe, molecular beacon probe or SERS-labeled probe.

21. The method of claim 1, wherein two or more target sequences or sequence variant nucleotide sequences are used concurrently, and wherein two or more nucleic acid signal primers which hybridize to said two or more target sequences are used.

22. The method of claim 1, wherein the two or more target sequences are present in the same contiguous nucleotide sequence or on two different nucleotide sequences.

23. The method of claim 3, wherein two or more target sequences or sequence variant nucleotide sequences are used concurrently, and wherein two or more nucleic acid signal primers which hybridize to said two or more target sequences are used.

24. The method of claim 3, wherein the two or more target sequences are present in the same contiguous nucleotide sequence or on two different nucleotide sequences.

25. The method of claim 3, wherein the first and second nucleic acid signal primers comprise a hybridization region and a reporter region.

26. The method of claim 3, wherein a second nucleic acid signal primer is hybridized to the second signal extension product, wherein the hybridized second nucleic acid signal primer is extended on the second signal extension product to produce a third signal extension product, wherein the third signal extension product has a hairpin structure on its 5' end, and wherein the second or the third signal extension product is detected in real time.

27. The method of claim 3, wherein a second nucleic acid signal primer is hybridized to the second signal extension product, wherein the hybridized second nucleic acid signal primer is extended on the second signal extension product to produce a third signal extension product, wherein the third signal extension product has a hairpin structure on its 5' end, and wherein the second or the third signal extension product is detected in a closed-tube format.

28. The method of claim 3, wherein a second nucleic acid signal primer is hybridized to the second signal extension product, wherein the hybridized second nucleic acid signal primer is extended on the second signal extension product to produce a third signal extension product, wherein the third signal extension product has a hairpin structure on its 5' end, and wherein the second or the third signal extension product is detected by providing a modification in the nucleic acid signal primer to facilitate capture of the signal extension product.

29. The method of claim 3, wherein a second nucleic acid signal primer is hybridized to the second signal extension product, wherein the hybridized second nucleic acid signal primer is extended on the second signal extension product to produce a third signal extension product, wherein the third signal extension product has a hairpin structure on its 5' end, and wherein the second or the third signal extension product is detected by a hybridization probe selected from the group consisting of fluorogenic probe, single nucleotide difference sensitive probe, molecular beacon probe or SERS-labeled probe.

* * * * *

SEQUENCE LISTING

<160> NUMBER OF SEQ ID NOS: 39

<210> SEQ ID NO 1
<211> LENGTH: 45
<212> TYPE: DNA
<213> ORGANISM: Artificial Sequence
<220> FEATURE:
<223> OTHER INFORMATION: Forward LAMP primer, FLP

<400> SEQUENCE: 1
accaccggcc ggatgttgga tgaccaccca ggacgtggag gcgat 45

<210> SEQ ID NO 2
<211> LENGTH: 44
<212> TYPE: DNA
<213> ORGANISM: Artificial Sequence
<220> FEATURE:
<223> OTHER INFORMATION: Reverse LAMP primer, RLP

<400> SEQUENCE: 2
ccggcggtct gtcacgtgaa ggccgtagtg tgacgggtgc acgt 44

<210> SEQ ID NO 3
<211> LENGTH: 25
<212> TYPE: DNA
<213> ORGANISM: Artificial Sequence
<220> FEATURE:
<223> OTHER INFORMATION: Forward outer primer, F3

<400> SEQUENCE: 3
cgggtcggca tgtcgcggat ggagc 25

<210> SEQ ID NO 4
<211> LENGTH: 26
<212> TYPE: DNA
<213> ORGANISM: Artificial Sequence
<220> FEATURE:
<223> OTHER INFORMATION: Reverse outer primer, R3

<400> SEQUENCE: 4
ccctcagggg tttcgatcgg gcacat 26

<210> SEQ ID NO 5
<211> LENGTH: 22
<212> TYPE: DNA
<213> ORGANISM: Artificial Sequence

```
<220> FEATURE:
<223> OTHER INFORMATION: Forward signal primer, FSP

<400> SEQUENCE: 5
cgccgcgatc aaggagttct tc                                          22

<210> SEQ ID NO 6
<211> LENGTH: 17
<212> TYPE: DNA
<213> ORGANISM: Artificial Sequence
<220> FEATURE:
<223> OTHER INFORMATION: Forward loop primer, FLoop(F4)

<400> SEQUENCE: 6
atcaacgtct gcggtgt                                                17

<210> SEQ ID NO 7
<211> LENGTH: 17
<212> TYPE: DNA
<213> ORGANISM: Artificial Sequence
<220> FEATURE:
<223> OTHER INFORMATION: Reverse loop primer, RLoop (R4)

<400> SEQUENCE: 7
ccgggctgga ggtccgc                                                17

<210> SEQ ID NO 8
<211> LENGTH: 49
<212> TYPE: DNA
<213> ORGANISM: Artificial Sequence
<220> FEATURE:
<223> OTHER INFORMATION: Forward LAMP primer for katG (FLP-kat)

<400> SEQUENCE: 8
cagcccaagc ccatctgctc cacatggcgc cggcccggcc gatctggtc             49

<210> SEQ ID NO 9
<211> LENGTH: 50
<212> TYPE: DNA
<213> ORGANISM: Artificial Sequence
<220> FEATURE:
<223> OTHER INFORMATION: Reverse LAMP primer fo katG (RLP-kat)

<400> SEQUENCE: 9
tatggacgaa cacccgacg aaagctccca ctcgtagccg tacaggatct             50

<210> SEQ ID NO 10
<211> LENGTH: 31
<212> TYPE: DNA
<213> ORGANISM: Artificial Sequence
<220> FEATURE:
<223> OTHER INFORMATION: Forward Outer primer for katG (F3-kat)

<400> SEQUENCE: 10
acagcggcgc tgatcgtcgg cggtcacact t                                31

<210> SEQ ID NO 11
<211> LENGTH: 26
<212> TYPE: DNA
<213> ORGANISM: Artificial Sequence
<220> FEATURE:
<223> OTHER INFORMATION: Reverse Outer primer for katG (R3-kat)

<400> SEQUENCE: 11
gcgccgtcct tggcggtgta ttgcca                                      26
```

```
<210> SEQ ID NO 12
<211> LENGTH: 16
<212> TYPE: DNA
<213> ORGANISM: Artificial Sequence
<220> FEATURE:
<223> OTHER INFORMATION: Forward Loop  primer for katG (F4-kat)

<400> SEQUENCE: 12
gagcagcctc gggttc                                                  16

<210> SEQ ID NO 13
<211> LENGTH: 18
<212> TYPE: DNA
<213> ORGANISM: Artificial Sequence
<220> FEATURE:
<223> OTHER INFORMATION: Reverse Loop primer for katG (R4-kat)

<400> SEQUENCE: 13
atgggacaac agtttcct                                                18

<210> SEQ ID NO 14
<211> LENGTH: 25
<212> TYPE: DNA
<213> ORGANISM: Artificial Sequence
<220> FEATURE:
<223> OTHER INFORMATION: Forward signal primer for katG (FSP-kat)

<400> SEQUENCE: 14
gtatggcacc ggaaccggta aggac                                        25

<210> SEQ ID NO 15
<211> LENGTH: 27
<212> TYPE: DNA
<213> ORGANISM: Artificial Sequence
<220> FEATURE:
<223> OTHER INFORMATION: Molecular beacon for katG (MBP-kat)
<220> FEATURE:
<221> NAME/KEY: misc_feature
<222> LOCATION: 1
<223> OTHER INFORMATION: n = dye1-C
<220> FEATURE:
<221> NAME/KEY: misc_feature
<222> LOCATION: 27
<223> OTHER INFORMATION: n = G-dabcyl

<400> SEQUENCE: 15
ncgaggcacc agcggcatcg acctggn                                      27

<210> SEQ ID NO 16
<211> LENGTH: 43
<212> TYPE: DNA
<213> ORGANISM: Artificial Sequence
<220> FEATURE:
<223> OTHER INFORMATION: Forward LAMP primer for inhA (FLP-inh)

<400> SEQUENCE: 16
acgtggctgc gatttccgga ccgacaaacg tcacgagcgt aac                    43

<210> SEQ ID NO 17
<211> LENGTH: 43
<212> TYPE: DNA
<213> ORGANISM: Artificial Sequence
<220> FEATURE:
<223> OTHER INFORMATION: Reverse LAMP primer for inhA (RLP-inh)

<400> SEQUENCE: 17
cacagccact gaaggggcca tcctccggta accaggactg aac                    43
```

```
<210> SEQ ID NO 18
<211> LENGTH: 20
<212> TYPE: DNA
<213> ORGANISM: Artificial Sequence
<220> FEATURE:
<223> OTHER INFORMATION: Forward Outer primer for inhA (F3-inh)

<400> SEQUENCE: 18
atccgtcatg gtcgaagtgt                                              20

<210> SEQ ID NO 19
<211> LENGTH: 20
<212> TYPE: DNA
<213> ORGANISM: Artificial Sequence
<220> FEATURE:
<223> OTHER INFORMATION: Reverse Outer primer for inhA (R3-inh)

<400> SEQUENCE: 19
gagccagccg ctgtgcgatc                                              20

<210> SEQ ID NO 20
<211> LENGTH: 15
<212> TYPE: DNA
<213> ORGANISM: Artificial Sequence
<220> FEATURE:
<223> OTHER INFORMATION: Forward Loop primer for inhA (F4-inh)

<400> SEQUENCE: 20
gggaactttc gcact                                                   15

<210> SEQ ID NO 21
<211> LENGTH: 15
<212> TYPE: DNA
<213> ORGANISM: Artificial Sequence
<220> FEATURE:
<223> OTHER INFORMATION: Reverse Loop primer for inhA (R4-inh)

<400> SEQUENCE: 21
acccccattc gtatc                                                   15

<210> SEQ ID NO 22
<211> LENGTH: 23
<212> TYPE: DNA
<213> ORGANISM: Artificial Sequence
<220> FEATURE:
<223> OTHER INFORMATION: Forward Signal primer for inhA (FSP-inh)

<400> SEQUENCE: 22
acgctcgtgg acataccgat ttc                                          23

<210> SEQ ID NO 23
<211> LENGTH: 28
<212> TYPE: DNA
<213> ORGANISM: Artificial Sequence
<220> FEATURE:
<223> OTHER INFORMATION: Molecular beacon inhA (MBP-inh)
<220> FEATURE:
<221> NAME/KEY: misc_feature
<222> LOCATION: 1
<223> OTHER INFORMATION: n = dye2-C
<220> FEATURE:
<221> NAME/KEY: misc_feature
<222> LOCATION: 28
<223> OTHER INFORMATION: n = G-dabcyl

<400> SEQUENCE: 23
```

```
ngaggccgac aacctatcgt ctccctcn                                          28
```

<210> SEQ ID NO 24
<211> LENGTH: 39
<212> TYPE: DNA
<213> ORGANISM: Artificial Sequence
<220> FEATURE:
<223> OTHER INFORMATION: Forward LAMP primer for gyrB (FLP-gyr)
<220> FEATURE:
<221> NAME/KEY: misc_feature
<222> LOCATION: 1
<223> OTHER INFORMATION: n = dye3-A

<400> SEQUENCE: 24

```
ngaccactcg tacccgtcgc cggtggttaa cgcgctatc                              39
```

<210> SEQ ID NO 25
<211> LENGTH: 20
<212> TYPE: DNA
<213> ORGANISM: Artificial Sequence
<220> FEATURE:
<223> OTHER INFORMATION: Quencher probe for gyrB (QP-gyr)
<220> FEATURE:
<221> NAME/KEY: misc_feature
<222> LOCATION: 20
<223> OTHER INFORMATION: n = T-dabcyl

<400> SEQUENCE: 25

```
gcgacgggta cgagtggtcn                                                   20
```

<210> SEQ ID NO 26
<211> LENGTH: 40
<212> TYPE: DNA
<213> ORGANISM: Artificial Sequence
<220> FEATURE:
<223> OTHER INFORMATION: Reverse LAMP primer for gyrB (RLP-gyr)

<400> SEQUENCE: 26

```
atgagaagtc ggaacccctg ggaccgttga ccccgtcttc                             40
```

<210> SEQ ID NO 27
<211> LENGTH: 19
<212> TYPE: DNA
<213> ORGANISM: Artificial Sequence
<220> FEATURE:
<223> OTHER INFORMATION: Forward Outer primer for gyrB (F3-gyr)

<400> SEQUENCE: 27

```
gcgatatctg gtggtctgc                                                    19
```

<210> SEQ ID NO 28
<211> LENGTH: 18
<212> TYPE: DNA
<213> ORGANISM: Artificial Sequence
<220> FEATURE:
<223> OTHER INFORMATION: Reverse Outer primer for gyrB (R3-gyr)

<400> SEQUENCE: 28

```
cgtggtttcg aaaacagc                                                     18
```

<210> SEQ ID NO 29
<211> LENGTH: 19
<212> TYPE: DNA
<213> ORGANISM: Artificial Sequence
<220> FEATURE:
<223> OTHER INFORMATION: Forward Loop primer for gyrB (F4-gyr)

<400> SEQUENCE: 29
ttgatctcga cttcgagcc                                              19

<210> SEQ ID NO 30
<211> LENGTH: 16
<212> TYPE: DNA
<213> ORGANISM: Artificial Sequence
<220> FEATURE:
<223> OTHER INFORMATION: Forward Loop primer for gyrB (R3-gyr)

<400> SEQUENCE: 30
cctcaagcaa ggggcg                                                 16

<210> SEQ ID NO 31
<211> LENGTH: 24
<212> TYPE: DNA
<213> ORGANISM: Artificial Sequence
<220> FEATURE:
<223> OTHER INFORMATION: Probe A for detecting mutations in the rpoB
      sequence contained in LAMP secondary products
<220> FEATURE:
<221> NAME/KEY: misc_feature
<222> LOCATION: 1
<223> OTHER INFORMATION: n = Texas red-TTTTTT-fluoresescein-C
<220> FEATURE:
<221> NAME/KEY: misc_feature
<222> LOCATION: 24
<223> OTHER INFORMATION: n = G-dabcyl

<400> SEQUENCE: 31
ngagctcagc tggctggtgc ctcn                                        24

<210> SEQ ID NO 32
<211> LENGTH: 31
<212> TYPE: DNA
<213> ORGANISM: Artificial Sequence
<220> FEATURE:
<223> OTHER INFORMATION: Probe B for detecting mutations in the rpoB
      sequence contained in LAMP secondary products
<220> FEATURE:
<221> NAME/KEY: misc_feature
<222> LOCATION: 1
<223> OTHER INFORMATION: n = tetrachlorofluorescein-G
<220> FEATURE:
<221> NAME/KEY: misc_feature
<222> LOCATION: 31
<223> OTHER INFORMATION: n = C-dabcyl

<400> SEQUENCE: 32
nctacgagcc aattcatgga ccagacgtag n                                31

<210> SEQ ID NO 33
<211> LENGTH: 28
<212> TYPE: DNA
<213> ORGANISM: Artificial Sequence
<220> FEATURE:
<223> OTHER INFORMATION: Probe C for detecting mutations in the rpoB
      sequence contained in LAMP secondary products
<220> FEATURE:
<221> NAME/KEY: misc_feature
<222> LOCATION: 1
<223> OTHER INFORMATION: n = tetramethylrhodamine-TTTTTT-fluorescein-C
<220> FEATURE:
<221> NAME/KEY: misc_feature
<222> LOCATION: 28
<223> OTHER INFORMATION: n = G-dabcyl

<400> SEQUENCE: 33
ncgacgccga cagcgggttg ttcgtcgn                                    28

```
<210> SEQ ID NO 34
<211> LENGTH: 26
<212> TYPE: DNA
<213> ORGANISM: Artificial Sequence
<220> FEATURE:
<223> OTHER INFORMATION: Probe D for detecting mutations in the rpoB
      sequence contained in LAMP secondary products
<220> FEATURE:
<221> NAME/KEY: misc_feature
<222> LOCATION: 1
<223> OTHER INFORMATION: n = rhodamine-TTTTTT-fluorescein-C
<220> FEATURE:
<221> NAME/KEY: misc_feature
<222> LOCATION: 26
<223> OTHER INFORMATION: n = G-dabcyl

<400> SEQUENCE: 34
ncacgcttgt gggtcaaccc ccgtgn                                          26

<210> SEQ ID NO 35
<211> LENGTH: 28
<212> TYPE: DNA
<213> ORGANISM: Artificial Sequence
<220> FEATURE:
<223> OTHER INFORMATION: Probe E for detecting mutations in the rpoB
      sequence contained in LAMP secondary products
<220> FEATURE:
<221> NAME/KEY: misc_feature
<222> LOCATION: 1
<223> OTHER INFORMATION: n = fluorescein-C
<220> FEATURE:
<221> NAME/KEY: misc_feature
<222> LOCATION: 28
<223> OTHER INFORMATION: n = G-dabcyl

<400> SEQUENCE: 35
nctgccgccg actgtcggcg ctggcagn                                        28

<210> SEQ ID NO 36
<211> LENGTH: 332
<212> TYPE: DNA
<213> ORGANISM: M. tuberculosis
<220> FEATURE:
<223> OTHER INFORMATION: sequence of rpoB target for LAMP (corresponds
      to Fig.7)

<400> SEQUENCE: 36
gagctgatcc aaaaccagat ccgggtcggc atgtcgcgga tggagcgggt ggtccgggag     60
cggatgacca cccaggacgt ggaggcgatc acaccgcaga cgttgatcaa catccggcgt    120
ggtcgccgcg atcaaggagt tcttcggcac cagccagctg agccaattca tggaccagca    180
acccgctgtc ggggttgacc cacaagcgcc gactgtcggc gctggggccc ggcggtctgt    240
cacgtgagcg tgccgggctg gaggtccgcg acgtgcaccc gtcgcactac ggccggatgt    300
gcccgatcga aaccctgag gggcccaaca tc                                   332

<210> SEQ ID NO 37
<211> LENGTH: 342
<212> TYPE: DNA
<213> ORGANISM: M. tuberculosis
<220> FEATURE:
<223> OTHER INFORMATION: sequence of katG target for LAMP (corresponds
      to Fig.8)

<400> SEQUENCE: 37
gaacgacgtc gaaacagcgg cgctgatcgt cggcggtcac actttcggta agacccatgg     60
cgccggcccg gccgatctgg tcggccccga accgaggct gctccgctgg agcagatggg    120
```

```
cttgggctgg aagagctcgt atggcaccgg aaccggtaag gacgcgatca ccagcggcat        180
cgaggtcgta tggacgaaca ccccgacgaa atgggacaac agtttcctcg agatcctgta        240
cggctacgag tgggagctga cgaagagccc tgctggcgct tggcaataca ccgccaagga        300
cggcgccggt gccggcacca tcccggaccc gttcggcggg cc                          342
```

<210> SEQ ID NO 38
<211> LENGTH: 300
<212> TYPE: DNA
<213> ORGANISM: M. tuberculosis
<220> FEATURE:
<223> OTHER INFORMATION: sequence of inhA target for LAMP (corresponds
      to Fig.9)

<400> SEQUENCE: 38

```
ccagaaaggg atccgtcatg gtcgaagtgt gctgagtcac accgacaaac gtcacgagcg         60 taacccagt gcgaaagttc cgccggaaa tcgcagccac gttacgctcg tggacatacc         120
gatttcggcc cggccgcggc gagacgatag gttgtcgggg tgactgccac agccactgaa        180
ggggccaaac ccccattcgt atcccgttca gtcctggtta ccggaggaaa ccggggatc         240 gggctggcga tcgcacagcg gctggctgcc gacggccaca aggtggccgt cacccaccgt        300
```

<210> SEQ ID NO 39
<211> LENGTH: 300
<212> TYPE: DNA
<213> ORGANISM: M. tuberculosis
<220> FEATURE:
<223> OTHER INFORMATION: sequence of gyrB target for LAMP (corresponds
      to Fig.10)

<400> SEQUENCE: 39

```
caactacatg ccggcggcaa gttcgactcg gacgcgtatg cgatatctgg tggtctgcac         60
ggcgtcggcg tgtcggtggt taacgcgcta tccacccggc tcgaagtcga gatcaagcgc        120
gacgggtacg agtggtctca ggtttatgag aagtcggaac ccctgggcct caagcaaggg        180
gcgccgacca agaagacggg gtcaacggtg cggttctggg ccgaccccgc tgttttcgaa        240
accacggaat acgacttcga aaccgtcgcc cgccggctgc aagagatggc gttcctcaac        300
```